US012630593B2

(12) United States Patent
Ding et al.

(10) Patent No.: US 12,630,593 B2
(45) Date of Patent: May 19, 2026

(54) METHOD OF KILLING LEUKEMIA CELLS BY ADMINISTRATION OF RECOMBINANT'Y3 PROTEINS

(71) Applicant: University of Florida Research Foundation, Incorporated, Gainesville, FL (US)

(72) Inventors: Yousong Ding, Gainesville, FL (US); Peilan Zhang, Gainesville, FL (US); Steven Douglas Bruner, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 621 days.

(21) Appl. No.: 18/050,485

(22) Filed: Oct. 28, 2022

(65) Prior Publication Data

US 2023/0272019 A1 Aug. 31, 2023

Related U.S. Application Data

(62) Division of application No. 16/633,993, filed as application No. PCT/US2018/043861 on Jul. 26, 2018, now Pat. No. 11,512,119.

(60) Provisional application No. 62/537,021, filed on Jul. 26, 2017.

(51) Int. Cl.
| | |
|---|---|
| *C07K 14/37* | (2006.01) |
| *A61K 38/16* | (2006.01) |
| *A61P 35/00* | (2006.01) |
| *A61P 35/02* | (2006.01) |
| *G01N 33/574* | (2006.01) |

(52) U.S. Cl.
CPC ............. *C07K 14/37* (2013.01); *A61K 38/16* (2013.01); *A61P 35/00* (2018.01); *A61P 35/02* (2018.01); *G01N 33/57484* (2013.01)

(58) Field of Classification Search
CPC .......... C07K 14/37; A61K 38/16; A61P 35/00
See application file for complete search history.

(56) References Cited

U.S. PATENT DOCUMENTS

| | | | |
|---|---|---|---|
| 11,512,119 | B2 | 11/2022 | Ding et al. |
| 2016/0207968 | A1 | 7/2016 | Goldberg et al. |

OTHER PUBLICATIONS

International Preliminary Report on Patentability mailed Feb. 6, 2020, in connection with PCT/US2018/043861.
International Search Report and Written Opinion mailed Nov. 30, 2018, in connection with PCT/US2018/043861.
GenBank Submission. Coprinus comatus strain 5.252 Y3 protein (y3) mRNA, complete cds. Accession No. GQ859168.1. Sep. 1, 2011, [Retrieved on Sep. 21, 2018], https://www.ncbi.nlm.nih.gov/nuccore/GQ859168.1?report=genbank.
Wang et al., Cloning of y3 gene encoding a tobacco mosaic virus inhibitor from Coprinus comatus and transformation to Nicotiana tabacum. Wei Sheng Wu Xue Bao. Feb. 2010;50(2):182-90. English Abstract.
Wu et al., Purification and activities of an alkaline protein from mushroom Coprinus comatus. Wei Sheng Wu Xue Bao. Dec. 2003;43(6):793-8. English Abstract.
Liu et al., Enhancing protein stability with extended disulfide bonds. Proc Natl Acad Sci U S A. May 24, 2016;113(21):5910-5. doi: 10.1073/pnas.1605363113. Epub May 9, 2016.
Abraham et al., Jurkat T cells and development of the T-cell receptor signalling paradigm. Nat Rev Immunol. Apr. 2004;4(4):301-8. doi: 10.1038/nri1330.

*Primary Examiner* — Elly-Gerald Stoica
(74) *Attorney, Agent, or Firm* — Wolf, Greenfield & Sacks, P.C.

(57) ABSTRACT

The subject invention pertains to compositions and methods for preparing and using recombinant proteins based on the fungal *Coprinus comatus* Y3 protein to control plant and animal viruses and microbes, and diagnose, prevent and treat cancers. Methods are disclosed using compositions comprising recombinant Y3 proteins to diagnose, prevent and/or treat cancer diseases based on recombinant Y3 protein interaction with glycans expressed on cancer cells.

12 Claims, 26 Drawing Sheets

Specification includes a Sequence Listing.

CAA GAT CCT TTG TCT TGC TAT GAC AAC TTT GGG AAT CGT
GAT GTT GCA GCA TGT GCT AGA TTC ATT GAC GAC TTT TGC
GAT ACC TTG ACA CCA AAC ATT TAC CGA CCA AGA GAT AAC
GGA CAG AGA TGT TAC GTC GTC AAT GGC CAT AAA TGC GAC
TTT ACC GTG TTC AAC ACC AAC AAT GGT GGT TCT CCC ATA
AGA GCT TCA ACT CCT AAC TGT AAG ACT GTT CTT AGA GCT
GCA GCT AAT CGT TGT CCA ACA GGT GGA AGA GGC AAG ATC
AAT CCT AGT GCT CCA TTC CTG TTT GCC ATT GAT CCG AAT
GAT GGA GAC TGT TCC ACT GAT TTT TAA

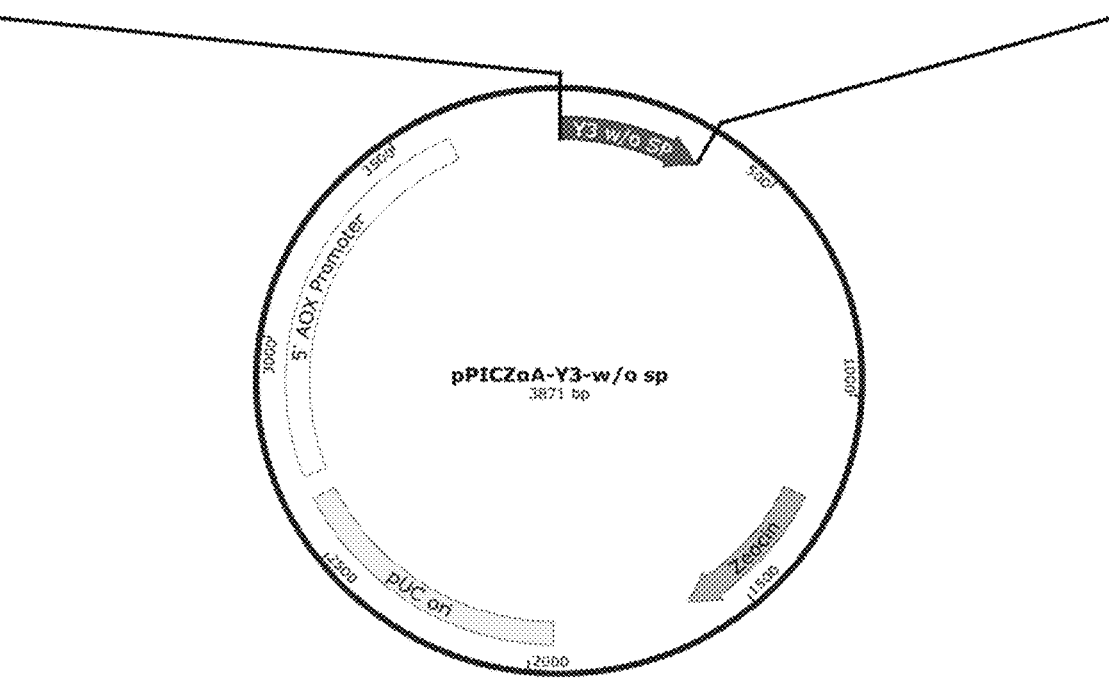

FIGURE 1A

QDPLSCYDNFGNRDVAACARFIDDFCDTLTPNIYRPRDNGQRCYV
VNGHKCDFTVFNTNNGGSPIRASTPNCKTVLRAAANRCPTGGRG
KINPSAPFLFAIDPNDGDCSTDF-

FIGURE 1B

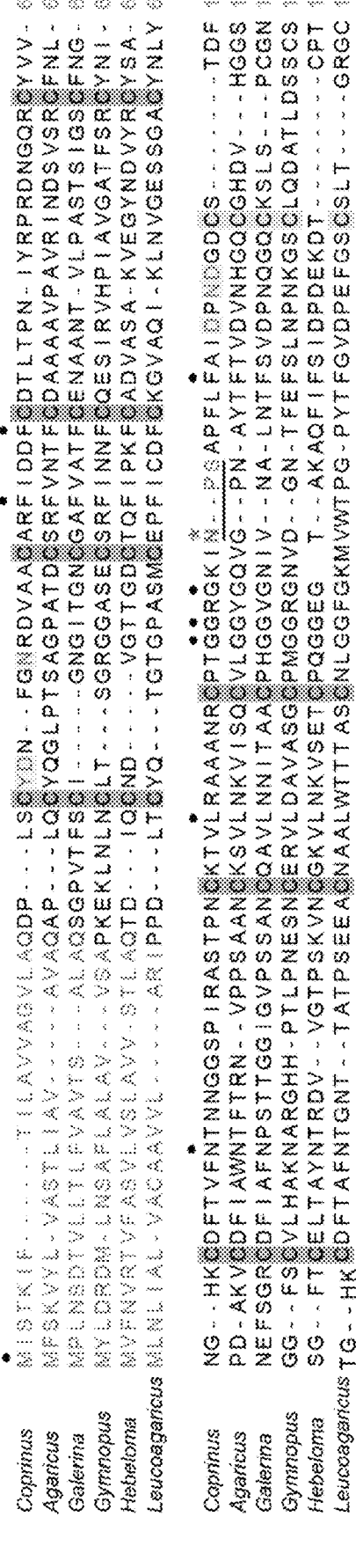
FIGURE 5A
FIGURE 5B
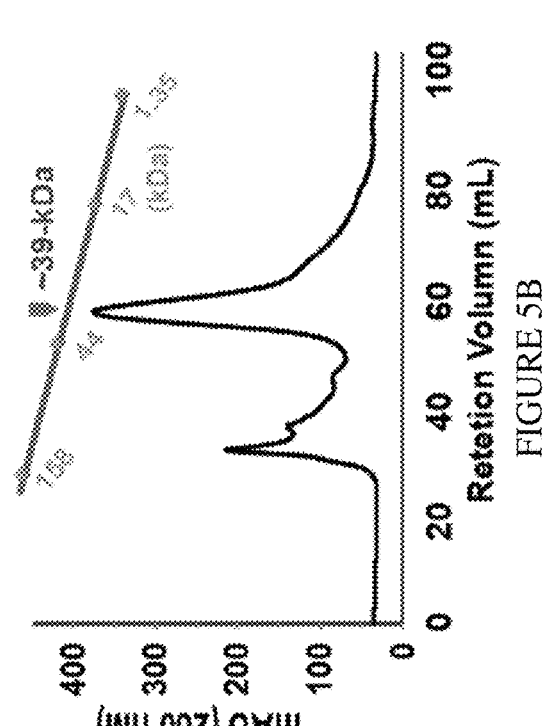
FIGURE 5C

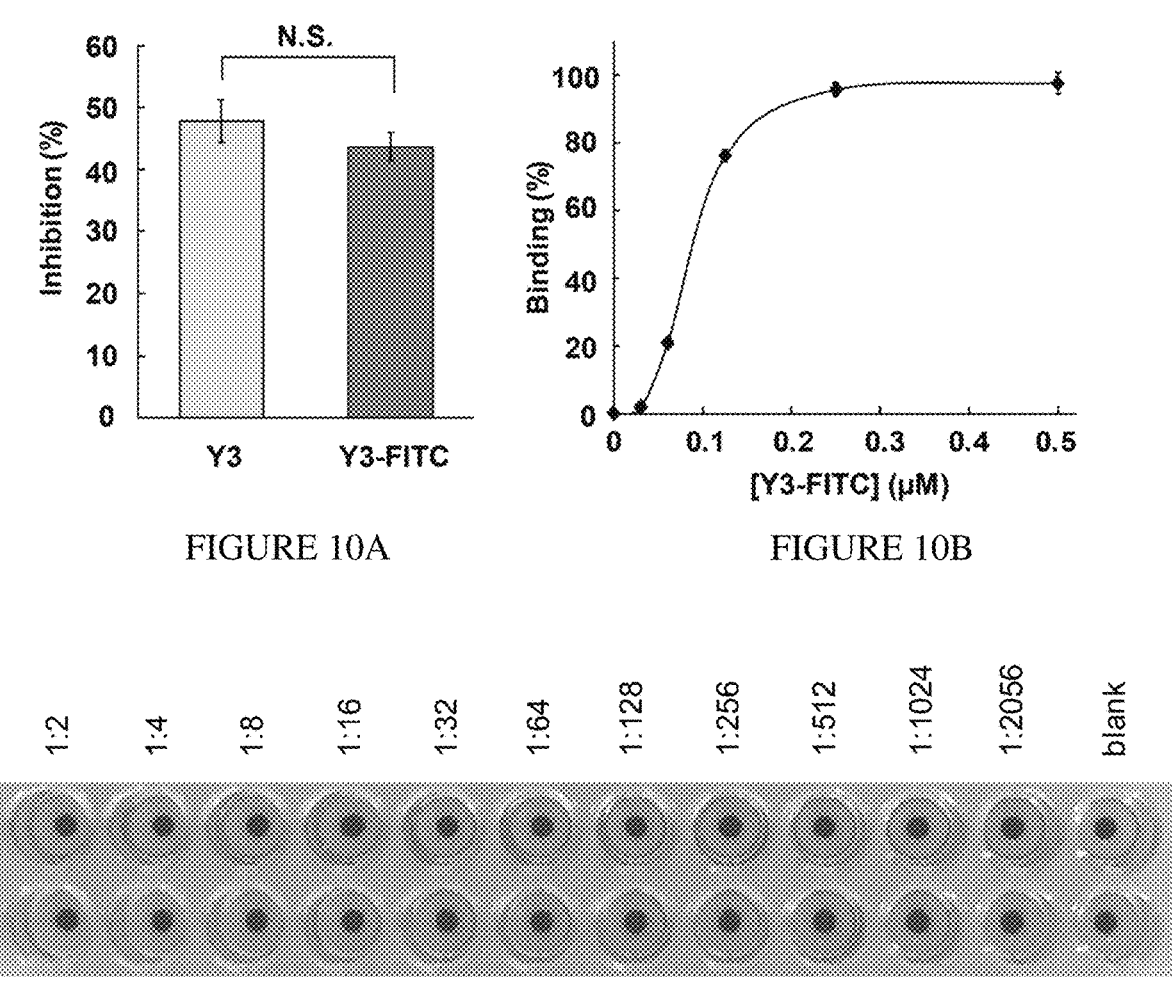
FIGURE 10A
FIGURE 10B
FIGURE 11
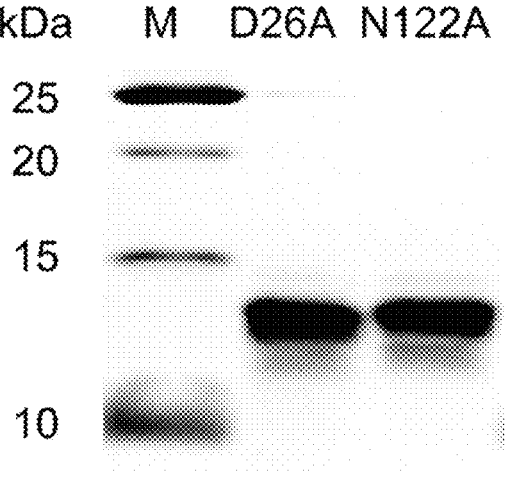
FIGURE 12

CNL

WFA

Interleukins

| Cont | Y3 | |
|------|-------|--------|
| 0.01 | 24.34 | IL3 |
| 0.01 | 1.20 | IL22 |
| 0.82 | 17.85 | IL2RA |
| 1.66 | 23.50 | IL21R |
| 0.52 | 3.53 | IL26 |
| 0.24 | 1.55 | IL1R1 |
| 1.44 | 9.06 | IL23A |
| 0.47 | 2.96 | IL2RB |
| 0.82 | 4.69 | IL7R |
| 0.35 | 1.83 | IL4I1 |
| 7.36 | 19.86 | IL4R |
| 7.49 | 16.94 | IL27RA | log$_2$(FPKM)]

Tumor necrosis factors (TNF)

| Cont | Y3 | |
|-------|--------|-----------|
| 0.01 | 3.16 | FASLG |
| 0.03 | 1.12 | TNFRSF18 |
| 0.08 | 2.00 | TNF |
| 6.21 | 132.26 | TNFSF14 |
| 2.33 | 43.39 | TRAF1 |
| 1.60 | 14.98 | TNFRSF12A |
| 6.27 | 46.47 | LTB |
| 1.07 | 5.12 | TNFSF9 |
| 3.37 | 8.72 | TNFRSF4 |
| 0.40 | 1.02 | TNFSF8 |
| 11.76 | 30.23 | TRAF4 |
| 10.25 | 23.32 | TNFAIP3 |
| 3.40 | 7.60 | LTA | log$_2$(FPKM)]

Chemokines

| Cont | Y3 | |
|------|-------|---------|
| 0.01 | 25.82 | CCL4L2 |
| 0.06 | 91.48 | CCL4 |
| 0.01 | 10.34 | CCL3 |
| 0.01 | 6.02 | XCL1 |
| 0.06 | 28.93 | XCL2 |
| 0.01 | 3.64 | CXCL8 |
| 0.01 | 1.73 | CCL3L1 |
| 0.19 | 10.71 | CCL20 |
| 1.13 | 30.28 | CXCR3 |
| 0.84 | 1.75 | CCRL2 | log$_2$(FPKM)]

FIGURE 20C

SEQUENCE LISTING

Sequence total quantity: 15
SEQ ID NO: 1                moltype = AA   length = 130
FEATURE                     Location/Qualifiers
source                      1..130
                            mol_type = protein
                            note = Coprinus comatus
                            organism = unidentified
SEQUENCE: 1
MISTKIFTIL AVVAGVLAQD PLSCYDNFGN RDVAACARFI DDFCDTLTPN IYRPRDNGQR   60
CYVVNGHKCD FTVFNTNNGG SPIRASTPNC KTVLRAAANR CPTGGRGKIN PSAPFLFAID  120
PNDGDCSTDF                                                         130

SEQ ID NO: 2                moltype = DNA   length = 339
FEATURE                     Location/Qualifiers
source                      1..339
                            mol_type = genomic DNA
                            note = Coprinus comatus
                            organism = unidentified
SEQUENCE: 2
caagatcctt tgtcttgcta tgacaacttt gggaatcgtg atgttgcagc atgtgctaga   60
ttcattgacg acttttgcga taccttgaca ccaaacattt accgaccaag agataacgga  120
cagagatgtt acgtcgtcaa tggccataaa tgcgacttta ccgtgttcaa caccaacaat  180
ggtggttctc ccataagagc ttcaactcct aactgtaaga ctgttcttag agctgcagct  240
aatcgttgtc caacaggtgg aagaggcaag atcaatccta gtgctccatt cctgtttgcc  300
attgatccga atgatggaga ctgttccact gattttaa                          339

SEQ ID NO: 3                moltype = AA   length = 112
FEATURE                     Location/Qualifiers
source                      1..112
                            mol_type = protein
                            note = Coprinus comatus
                            organism = unidentified
SEQUENCE: 3
QDPLSCYDNF GNRDVAACAR FIDDFCDTLT PNIYRPRDNG QRCYVVNGHK CDFTVFNTNN   60
GGSPIRASTP NCKTVLRAAA NRCPTGGRGK INPSAPFLFA IDPNDGDCST DF          112

SEQ ID NO: 4                moltype = DNA   length = 30
FEATURE                     Location/Qualifiers
misc_feature               1..30
                            note = Primer Y3FxH
source                      1..30
                            mol_type = other DNA
                            organism = synthetic construct
SEQUENCE: 4
gtatctctcg agaaaagaca agatcctttg                                    30

SEQ ID NO: 5                moltype = DNA   length = 32
FEATURE                     Location/Qualifiers
misc_feature               1..32
                            note = Primer Y3RNt
source                      1..32
                            mol_type = other DNA
                            organism = synthetic construct
SEQUENCE: 5
ttttcctttt gcggccgctt aaaaatcagt gg                                 32

SEQ ID NO: 6                moltype = DNA   length = 36
FEATURE                     Location/Qualifiers
misc_feature               1..36
                            note = Primer D26AFw
source                      1..36
                            mol_type = other DNA
                            organism = synthetic construct
SEQUENCE: 6
tgctatgcca actttgggaa tcgtgatgtt gcagca                             36

SEQ ID NO: 7                moltype = DNA   length = 36
FEATURE                     Location/Qualifiers
misc_feature               1..36
                            note = Primer D26ARv
source                      1..36
                            mol_type = other DNA
                            organism = synthetic construct
SEQUENCE: 7
tgctgcaaca tcacgattcc caaagttggc atagca                             36

SEQ ID NO: 8                moltype = DNA   length = 36
FEATURE                     Location/Qualifiers -continued

```
misc_feature          1..36
                      note = Primer N122AFw
source                1..36
                      mol_type = other DNA
                      organism = synthetic construct
SEQUENCE: 8
gatccggctg atggagactg ttccactgat ttttaa                              36

SEQ ID NO: 9          moltype = DNA  length = 36
FEATURE               Location/Qualifiers
misc_feature          1..36
                      note = Primer N122ARv
source                1..36
                      mol_type = other DNA
                      organism = synthetic construct
SEQUENCE: 9
ttaaaaatca gtggaacagt ctccatcagc cggatc                              36

SEQ ID NO: 10         moltype = AA  length = 130
FEATURE               Location/Qualifiers
source                1..130
                      mol_type = protein
                      note = Coprinus
                      organism = unidentified
SEQUENCE: 10
MISTKIFTIL AVVAGVLAQD PLSCYDNFGN RDVAACARFI DDFCDTLTPN IYRPRDNGQR    60
CYVVNGHKCD FTVFNTNNGG SPIRASTPNC KTVLRAAANR CPTGGRGKIN PSAPFLFAID    120
PNDGDCSTDF                                                          130

SEQ ID NO: 11         moltype = AA  length = 135
FEATURE               Location/Qualifiers
source                1..135
                      mol_type = protein
                      note = Agaricus
                      organism = unidentified
SEQUENCE: 11
MFSKVYLVAS TLIAVAVAQA PLQCYQGLPT SAGPATDCSR FVNTFCDAAA AVPAVRINDS    60
VSRCFNLPDA KVCDFIAWNT FTRNVPPSAA NCKSVLNKVI SQCVLGGYGQ VGPNAYTFTV    120
DVNHGQCGHD VHGGS                                                     135

SEQ ID NO: 12         moltype = AA  length = 138
FEATURE               Location/Qualifiers
source                1..138
                      mol_type = protein
                      note = Galerina
                      organism = unidentified
SEQUENCE: 12
MPLNSDTVLL TLFVAVTSAL AQSGPVTFSC IGNGITGNCG AFVATFCENA ANTVLPASTS    60
IGSCFNGNEF SGRCDFIAFN PSTTGGIGVP SSANCQAVLN NITAACPHGG VGNIVNALNT    120
FSVDPNQGQC KSLSPCGN                                                  138

SEQ ID NO: 13         moltype = AA  length = 140
FEATURE               Location/Qualifiers
source                1..140
                      mol_type = protein
                      note = Gymnopus
                      organism = unidentified
SEQUENCE: 13
MYLDRDMLNS AFLALAVVSA PKEKLNLNCL TSGRGGASEC SRFINNFCQE SIRVHPIAVG    60
ATFSRCYNIG GFSCVLHAKN ARGHHPTLPN ESNCERVLDA VASGCPMGGR GNVDGNTFEF    120
SLNPNKGSCL QDATLDSSCS                                                140

SEQ ID NO: 14         moltype = AA  length = 127
FEATURE               Location/Qualifiers
source                1..127
                      mol_type = protein
                      note = Hebeloma
                      organism = unidentified
SEQUENCE: 14
MVFNVRTVFA SVLVSLAVVS TLAQTDIQCN DVGTTGDCTQ FIPKFCADVA SAKVEGYNDV    60
YRCYSASGFT CELTAYNTRD VVGTPSKVNC GKVLNKVSET CPQGGEGTAK AQFIFSIDPD    120
EKDTCPT                                                              127

SEQ ID NO: 15         moltype = AA  length = 132
FEATURE               Location/Qualifiers
source                1..132
                      mol_type = protein
                      note = Leucoagaricus
                      organism = unidentified
```

-continued

```
SEQUENCE: 15
MLNLIALVAC AAVVLARIPP DLTCYQTGTG PASMCEPFIC DFCKGVAQIK LNVGESSGAC   60
YNLYTGHKCD FTAFNTGNTT ATPSEEACNA ALWTTTASCN LGGFGKMVWT PGPYTFGVDP  120
EFGSCSLTGR GC                                                      132
```

METHOD OF KILLING LEUKEMIA CELLS BY ADMINISTRATION OF RECOMBINANT'Y3 PROTEINS

CROSS-REFERENCE TO RELATED APPLICATION

This application is a Division of U.S. application Ser. No. 16/633,993, filed Jan. 24, 2020, which is a National Stage filing under 35 U.S.C. 371 of International Patent Application No. PCT/US2018/043861, filed Jul. 26, 2018, which claims priority to U.S. Provisional Application No. 62/537, 021, filed Jul. 26, 2017. The entire content of the foregoing applications are expressly incorporated herein by reference.

REFERENCE TO AN ELECTRONIC SEQUENCE LISTING

The contents of the electronic sequence listing (U119570138US02-SEQ-KZM.xml; Size: 19,347 bytes; and Date of Creation: Oct. 24, 2022) is herein incorporated by reference in its entirety.

BACKGROUND OF THE INVENTION

Polysaccharides (glycans) are a fundamental building block of life, ubiquitously expressed in all organisms and essential to numerous biological processes including adhesion and growth, signaling, infection, and tumor pathogenesis (1-3). In addition, aberrant glycosylation is directly linked with many human diseases (4). Of note, glycans serve as useful biomarkers of various cancers and targets of therapeutic intervention (4-7). Glycan binding proteins (GBPs) read the diversity and complexity of glycans in a relatively specific manner and execute the physiological or pathological information encoded by the polymers (1, 8). The specificity of GBP-glycan interactions are determined by multiple factors including composition, site-specific modifications and tertiary structure of the glycans. Lectins form one major group of GBPs and are widely distributed among organisms (e.g., viruses, bacteria, fungi, insects, plants, and animals) (9, 10). Lectins adopt at least 14 different folds and common examples include the ricin-like β-trefoil, galectin-like fold, actinoporin-like fold, and β-propeller (11, 12). However, folds can show low sequence identities amongst family members (13). Indeed, significant diversity in sequence and folds highlights the divergent and convergent evolution of protein functions and poses challenges to accurately and reliably annotate new members (14, 15).

A number of GBPs are small proteins, less than 150 amino acids. Over the past decades the functions of many small proteins have been discovered to be critical to various cellular processes, primarily through serendipitous studies (16). For example, galectin-1 with an affinity for β-galactose (Gal) was shown to be essential to neuronal cell differentiation and be associated with malignant tumor progression in human (17, 18). Small proteins also regulate essential cellular processes of bacteria (e.g., the 43-aa SgrS) (19), yeast (20), and animals (16). In recent years, systems biology studies have demonstrated that organisms commonly express hundreds of small proteins that often have no characterized homologs (16, 21-23). Accurately assigning a biochemical, cellular or physiological function to these proteins is a rapidly evolving research area whose advances require the integration of multiple disciplines (16, 24).

Leukemia is among the top five common causes of cancer deaths in the U.S. (25). As a subtype, T-cell acute lymphoblastic leukemia (T-ALL) is an aggressive hematological malignancy that accounts for 10-15% of pediatric and 20-25% of adult cases of ALL (26, 27). With intensified chemotherapy protocols, the current five-year relative survival rates of T-ALL that is diagnosed in early stages reach above 60%. However, the long-term survival of T-ALL patients remains extremely poor due to the remission and recurrence rate (26, 28). Development of new therapeutics and early detection tools is of significance to the management of T-ALL. Over recent years, substantial advances in leukemia biology have been attained (29) and are providing opportunities for more selective and effective treatment. For example, the apoptosis of leukemic T-cells can be controlled precisely by targeting cell-surface glycoproteins (e.g., CD95) (30).

Mushrooms have been used for food, medicine or other purposes for thousands of years (31) but 90% of mushroom species in nature remain unexplored (32, 33). The potential of this untapped source in the discovery of useful substances is exemplified by the semisynthetic analog of pleuromutilin (retapamulin) as clinically used antibiotic (34), illudins as anticancer drugs (35), and peptidic omphalotins as nematicidal agents (36). In addition to low molecular weight (MW) secondary metabolites, mushrooms produce a variety of proteins, such as lectins, with antitumor, antiviral, antimicrobial, antioxidative, and/or immunomodulatory activities (37). Recent genomic and computational studies have further identified an enormous number of genes encoding small proteins from fungal genomes (38). These small proteins awaiting assigned functions can become useful biotechnological and biomedical agents (37).

Y3 is a 130-aa protein isolated from the edible mushroom *Coprinus comatus* and initial characterization showed that it inhibits the infection and multiplication of the tobamovirus, Tobacco mosaic virus (TMV) (39). A search of public available genome databases yielded a limited number of Y3 homologs with only low sequence similarity, none of which had been characterized.

BRIEF SUMMARY OF THE INVENTION

Provided are compositions comprising recombinant Y3 proteins based on the fungal *Coprinus comatus* Y3 protein and variants thereof. Further provided are methods for preparing said compositions and the use of said compositions for the diagnosis, prevention and/or treatment of diseases caused by microbes, and viruses, cancer diseases and infertility. The recombinant Y3 proteins of the compositions can be also used as delivery carriers to deliver marker molecules for diagnosis applications and therapeutic molecules for prevention and treatment applications.

The methods of detecting microbes, viruses or cancer cells provided herein comprise administering to a subject a composition comprising recombinant Y3 proteins labeled with a marker molecule and detecting the marker molecule.

The methods of preventing and/or treating a disease caused by microbes, viruses, or a cancer disease comprise administering a composition comprising the recombinant Y3 protein or variants thereof either unconjugated or conjugated to one or more therapeutic moieties or molecules.

BRIEF DESCRIPTION OF THE DRAWINGS

FIG. 1A shows a map of the synthesized, codon-optimized nucleic acid sequence of SP-free Y3 (SEQ ID NO: 2).

FIG. 1B shows the amino acid sequence of the mature recombinant Y3 protein (SEQ ID NO: 3).

FIG. 5A shows a sequence alignment of Y3 and its homologues from other fungal species (*Coprinus*, SEQ ID NO: 10; *Agaricus*, SEQ ID NO: 11; *Galerina*, SEQ ID NO: 12; *Gymnopus*, SEQ ID NO: 13; *Hebeloma*, SEQ ID NO: 14; and *Leucoagaricus*, SEQ ID NO: 15). FIG. 5B shows size exclusion chromatographic analysis of recombinant Y3. FIG. 5C shows SDS PAGE analysis of recombinant Y3.

FIG. 10A shows comparable anti-Jurkat activity of Y3 and Y3-FITC. FIG. 10B shows dose-dependent binding of Y3-FITC to Jurkat cells.

FIG. 11 shows a hemagglutination assay of Y3 using human (upper panel) and rabbit (lower panel) erythrocytes.

FIG. 12 shows a SDS-PAGE analysis of purified Y3D26A and Y3N122A.

FIGS. 20A-20C show RNA-seq analysis of Y3 treated Jurkat cells. This analysis indicates that Y3 likely induces the activation of Jurkat cells. FIG. 20A shows the comparison of the gene expression profiles between Y3 treatment and control (PBS) groups, which revealed 2068 differentially expressed genes (DEGs), including 623 up-regulated and 1445 down-regulated genes. FIG. 20B shows that GO analysis clustered DEGs into ten terms that are related to T-cell activation. FIG. 20C shows that the expression of a number of cytokines was upregulated in Y3 treated Jurkat cells compared to control treated Jurkat cells.

BRIEF DESCRIPTION OF THE SEQUENCES

Figure 2:
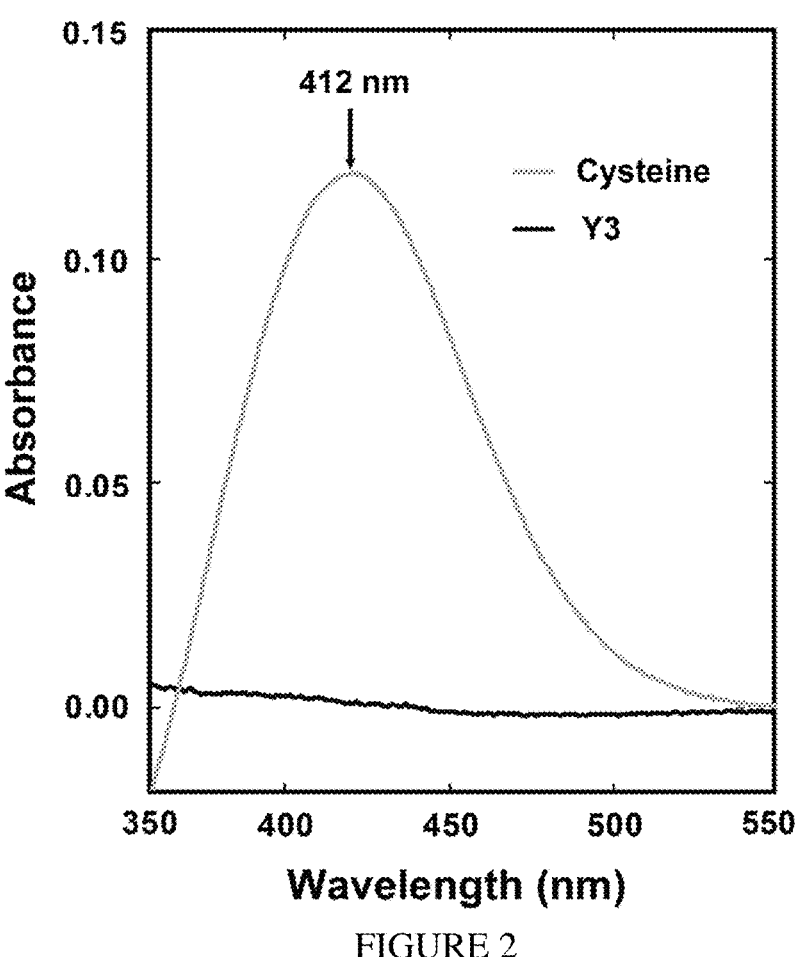
FIG. 2 shows a UV-vis spectral analysis of the Ellman's test for Y3.

SEQ ID NO: 1 shows the amino acid sequence of *Coprinus comatus* Y3 protein (Genbank Accession No. ADK35888.1).

SEQ ID NO: 2 shows the nucleic acid sequence of the codon-optimized, synthesized nucleotide sequence encoding recombinant Y3.

SEQ ID NO: 3 shows the amino acid sequence of SP-free recombinant Y3.

SEQ ID NO: 4 shows the sequence of primer Y3FXh.

SEQ ID NO: 5 shows the sequence of primer Y3RNt.

SEQ ID NO: 6 shows the sequence of primer D26AFw.

SEQ ID NO: 7 shows the sequence of primer D26ARv.

SEQ ID NO: 8 shows the sequence of primer N122AFw.

SEQ ID NO: 9 shows the sequence of primer N122ARv.

DETAILED DISCLOSURE OF THE INVENTION

Provided herein are compositions and methods for preparing and using *Coprinus comatus* Y3 protein to control plant and animal viruses and microbes, and diagnose, prevent and treat cancers. The compositions and methods of the subject invention are based on the unexpected discovery that a recombinant Y3 protein based on a protein from the mushroom *Coprinus comatus* can provide antiviral activity against tobamovirus, can bind to LDNF glycan present on cells and viruses, and can induce apoptosis in human cancer cells.

In further embodiments, the compositions and methods of the subject invention can provide methods to detect, prevent and/or treat infertility.

In preferred embodiments, the compositions and methods of the subject invention relate to a recombinant Y3 protein that lacks an 18-amino acid N-terminal signaling peptide (SP). It has advantageously been discovered that said SP-free recombinant Y3 protein is more effective than native *Coprinus comatus* Y3 protein in providing anti-viral and anti-cancer activity. In other embodiments, a full-length Y3 protein from the mushroom *Coprinus comatus* can be used in the compositions and methods of the subject invention. In yet other embodiments, the recombinant Y3 protein is conjugated to molecules that include, but are not limited, to marker molecules, cytotoxic molecules, and therapeutic molecules. Marker molecules are known in the art and include, but are not limited to, molecules that are radioactive or emit fluorescence or molecules that enzymatically convert an inactive precursor into an active, signal emitting molecule. "Marker molecules" include, for example, $^{32}P$, $^{35}S$, various other radioisotopes, fluorescent dyes, electron-dense reagents, and enzymes.

In certain embodiments, the compositions and methods of the subject invention relate to a recombinant Y3 protein that lacks from the N-terminus one or more amino acid residues before the first cysteine residue that forms the multiple disulfide bridges, i.e., the first cysteine residue is retained in the recombinant Y3 protein. For example, if the first cysteine residue is the $24^{th}$ residue of a Y3 protein, a recombinant Y3 protein can lack from the N-terminus 1 up to 23 amino acids.

In certain other embodiments, the compositions and methods of the subject invention relate to a recombinant Y3 protein that lacks from the C-terminus one or more amino acids beyond the last cysteine residue that forms the multiple disulfide bridges, i.e., the last cysteine residue is retained in the recombinant Y3 protein. For example, if the last cysteine residue is the $126^{th}$ residue of a Y3 protein, a recombinant Y3 protein can lack from the C-terminus one or more amino acids beyond the cysteine at the $126^{th}$ position.

In even further embodiments, the compositions and methods of the subject invention relate to a recombinant Y3 protein that lacks from the N-terminus one or more amino acids before the first cysteine residue that forms the multiple disulfide bridges and/or lacks from the C-terminus one or more amino acids beyond the last cysteine residue that forms the multiple disulfide bridges, i.e., the first and the last cysteine residues are retained in the recombinant protein.

Thus, certain embodiments of the invention provide a recombinant Y3 protein, which is a truncated form of a Y3 protein and comprises the amino acids sequence between the first cysteine and the last cysteine that form the multiple disulfide bridges of the protein. A skilled artisan can produce such truncated proteins based on this disclosure, for example, from the sequence alignment provided in FIG. 5A. Additionally, a skilled artisan can determine such recombinant proteins based on this disclosure and a sequence of a Y3 protein, for example, by aligning the Y3 protein with the sequences provided in FIG. 5A.

In specific embodiments, the compositions and methods of the subject invention relate to a recombinant Y3 protein, which is a truncated form of *Coprinus comatus* Y3 protein having the sequence of SEQ ID NO: 1. In certain such embodiments, a recombinant Y3 protein lacks from the N-terminus 1 up to 23 amino acid residues of SEQ ID NO: 1. In additional such embodiments, a recombinant Y3 protein lacks from the C-terminus one or more amino acids beyond the cysteine at the $126^{th}$ position of SEQ ID NO: 1. In further such embodiments, a recombinant Y3 protein lacks from the N-terminus 1 up to 23 amino acid residues of SEQ ID NO: 1 and/or lacks from the C-terminus one or more amino acids beyond the cysteine at the $126^{th}$ position of SEQ ID NO: 1. For example, a recombinant Y3 protein comprises amino acid sequence from cysteine at $24^{th}$ position to the cysteine at the $126^{th}$ position of SEQ ID NO: 1.

In certain embodiments, the recombinant Y3 proteins can be conjugated to therapeutic molecules. In further embodiment, the recombinant Y3 proteins are fusion proteins with proteins that are able to convert a nontoxic prodrug into a toxic drug. Non-limiting examples of such proteins and prodrugs are Herpes simplex virus thymidine kinase (HSV-tk)/acyclovir (ACV) or ganciclovir (GCV), and the bacterial or fungal cytosine deaminase (CD)/5-florocytosine (5-FC).

In further embodiment, the recombinant Y3 proteins are fusion proteins with therapeutically relevant small molecular weight entities and biological substances, including antibodies, enzymes, vaccines, proteins, nucleic acids, aptamers, blood components, cells, allergens, toxins, cytokines, and mimics, such as peptidomimetics and nucleomimetics. In preferred embodiments, the therapeutically relevant molecule prevents and/or treats an infection with a microbe or a virus, prevent and/or treat the proliferation of cancer cells and/or prevent and/or treat infertility.

Specific examples of therapeutically relevant molecules that can be conjugated to Y3 protein include antisense oligonucleotides, doxorubicin, 5-fluorouracil, methotrexate, pyrrolobenzodiazepine, calicheamicin, maytanisinoid, ausristatins (e.g., monomethylauristatin E or monomethyl-auristatin F), pyrrolobenzodiazepines, mertansine/emtansine, ravtansine/soravtansine, vincristine, vinblastine, etoposide, melphalan, mitomycin C, chlorambucil, daunorubicin, ricin, a thalidomide or a thalidomide analog (e.g., lenalidomide, CC-3052, CC-4047, CC-5103, IMiD3, EM12, ENMD0995), dolastatin, trichothecene, enediynes, taxane, anthracycline, adriamycin, vindesine, vinca alkaloid, teniposide, carminomycin, aminopterin, dactinomycin, bleomycin, esperamicin, tubulysin, cryptophycins, erlotinib, bortezomib, fulvestrant, sunitinib, letrozole, imatinib mesylate, oxaliplatin, leucovorin, rapamycin, lapatinib, lonafarnib, sorafenib, gefitinib, capecitabine, duocarmycin, lexitropsin, nitrosourea, platinol, purine antimetabolite, puromycin, steroid, purine antagonist, androgen, 5-azacytidine, azathioprine, busulfan, buthionine sulfoximine, camptothecin, carboplatin, carmustine, estrogen, 5-fluordeoxyuridine, gramicidin D, hydroxyurea, idarubicin, ifosfamide, irinotecan, lomustine, mechlorethamine, mithramycin, mitoxantrone, nitroimidazole, plicamycin, procarbizine, streptozotocin, tenoposide, 6-thioguanine, topotecan, vinorelbine, acyclovir, gangcyclovir, zidovudine, vidarabine, ribavarin, azidothymidine, cytidine arabinoside, amantadine, didexoyuridine, iododeoxyuridine, poscarnet, and trifluridine.

Further provided are compositions that comprise recombinant Y3 proteins produced in yeast expression systems. In some embodiments, the recombinant Y3 proteins are produced in yeast expression system including, but not limited to, organisms from the genera *Saccharomyces, Pichia, Kluyveromyces, Hansenula,* Arxula adeninivorans, and *Yarrowia*. In other embodiments, any cell-based and cell-free expression system that enables heterologous protein expression and/or mammalian-like post-translational modification is used to generate recombinant Y3 proteins of the subject invention.

Cell-free expression systems are known in the art and typically derived from cell extracts of *Escherichia coli* S30, rabbit reticulocytes or wheat germ. Such system comprise one or more components selected from: a template nucleic acid encoding the Y3 protein, ribosomes, initiation factors (IF1, IF2, IF3), elongation factors (EF-Tu, EF-Ts, EF-G), release factors (RF1, RF2, RF3), ribosome recycling factor, 20 Aminoacyl tRNA synthetases, methionyl tRNA formyltransferase, tRNAs, energy regeneration system, NTPs, amino acids, salts and buffers. Various expression systems for cell-free expression of Y3 protein can be readily designed by a person of ordinary skill in the art based on the knowledge in the relevant and such embodiments are within the purview of the invention.

In further embodiments, the subject invention provides genetic constructs that are used to express recombinant Y3 proteins. The genetic constructs of the subject invention include at least one expression cassette comprising regulatory sequences to provide expression of the polypeptides in cells of the respective expression system. Expression constructs and vectors to be used to express the polypeptides of the invention in the respective expression system are based on the expression system used and are readily available to a person with ordinary skill in the art having the benefit of the instant disclosure.

Methods for preparing compositions of the subject invention comprising recombinant Y3 proteins are provided. Although preferred methods of preparing compositions of the subject invention comprising recombinant Y3 proteins are provided herein, recombinant Y3 proteins can be expressed and purified using any method of protein purification known to the person with ordinary skill in the art.

In certain embodiments, the Y3 protein disclosed herein is used as a carrier for delivery of a therapeutic or diagnostic molecule to a target cell, particularly, a target cell expressing a glycan receptor to which the Y3 protein binds. Accordingly, certain embodiments of the invention provide a method of delivering a therapeutic or diagnostic molecule to a target cell by contacting the target cell with a Y3 protein conjugated to the therapeutic or diagnostic molecule.

Non-limiting examples of therapeutic and diagnostic molecules that can be delivered to a target cell using Y3 protein include with therapeutically relevant small molecular weight entities and biological substances, including antibodies, enzymes, vaccines, proteins, nucleic acids, aptamers, blood components, cells, allergens, toxins, cytokines, and mimics, such as peptidomimetics and nucleomimetics. In preferred embodiments, the therapeutically relevant molecules prevent and/or treat an infection with a microbe or a virus, prevent and/or treat the proliferation of cancer cells and/or prevent and/or treat infertility.

Specific examples of molecules that can be conjugated to Y3 protein include antisense oligonucleotides, doxorubicin, 5-fluorouracil, methotrexate, pyrrolobenzodiazepine, calicheamicin, maytanisinoid, ausristatins (e.g., monomethylauristatin E or monomethylauristatin F), pyrrolobenzodiazepines, mertansine/emtansine, ravtansine/soravtansine, vincristine, vinblastine, etoposide, melphalan, mitomycin C, chlorambucil, daunorubicin, ricin, a thalidomide or a thalidomide analog (e.g., lenalidomide, CC-3052, CC-4047, CC-5103, IMiD3, EM12, ENMD0995), dolastatin, trichothecene, enediynes, taxane, anthracycline, adriamycin, vindesine, vinca alkaloid, teniposide, carminomycin, aminopterin, dactinomycin, bleomycin, esperamicin, tubulysin, cryptophycins, erlotinib, bortezomib, fulvestrant, sunitinib, letrozole, imatinib mesylate, oxaliplatin, leucovorin, rapamycin, lapatinib, lonafarnib, sorafenib, gefitinib, capecitabine, duocarmycin, lexitropsin, nitrosourea, platinol, purine antimetabolite, puromycin, steroid, purine antagonist, androgen, 5-azacytidine, azathioprine, busulfan, buthionine sulfoximine, camptothecin, carboplatin, carmustine, estrogen, 5-fluordeoxyuridine, gramicidin D, hydroxyurea, idarubicin, ifosfamide, irinotecan, lomustine, mechlorethamine, mithramycin, mitoxantrone, nitroimidazole, plicamycin, procarbizine, streptozotocin, tenoposide, 6-thioguanine, topotecan, vinorelbine, acyclovir, gangcyclovir, zidovudine, vidarabine, ribavarin, azidothymidine, cytidine arabinoside, amantadine, dideoxyuridine, iododeoxyuridine, poscarnet, and trifluridine.

In preferred embodiments the subject invention provides methods for assessing the presence of microbes or viruses in a subject, the method comprising administering a composition of the subject invention to a subject suspected of hosting microbes or viruses, which microbes or viruses are known to be capable of inducing a disease in the subject, wherein the composition comprises a recombinant Y3 protein conjugated to a detectable marker prepared according to the subject invention and wherein the interaction of the recombinant Y3 protein with the microbes or viruses in the subject is detected by detection of the marker in the subject. In preferred embodiments, the marker conjugated to the recombinant Y3 protein is a marker that emits a signal that can be detected from or is detectable from the surface of the subject.

In other embodiments, the subject invention provides methods for assessing the presence of a cancer disease in a subject, the method comprising administering a composition of the subject invention to a subject suspected of suffering from a cancer disease, wherein the composition comprises a recombinant Y3 protein conjugated to a detectable marker prepared according to the subject invention and wherein the interaction of the recombinant Y3 protein with cancer cells in the subject is detected by detection of the marker in the subject. In preferred embodiments, the marker conjugated to the recombinant Y3 protein is a marker that emits a signal that can be detected from the surface of the subject.

In further embodiments, the methods for assessing the presence of microbes or viruses in a subject comprise obtaining a biological sample from a subject suspected of suffering from a disease caused by microbes or a viruses, contacting the biological sample with a composition of the subject invention, which composition comprises a recombinant Y3 protein conjugated to a detectable marker prepared according to the subject invention and wherein the interaction of the recombinant Y3 protein with the microbes or viruses in the biological sample of the subject is detected by the presence of the marker in the biological sample. In some embodiments, the method includes steps of separating the marker bound material from the non-bound material in the biological sample.

In further embodiments, the methods for assessing the presence of cancer cells in a subject comprise obtaining a biological sample from a subject suspected of suffering from a cancer disease, contacting the biological sample with a composition of the subject invention, which composition comprises a recombinant Y3 protein conjugated to a detectable marker prepared according to the subject invention and wherein the interaction of the recombinant Y3 protein with the cancer cells in the biological sample of the subject is detected by the presence of the marker in the biological sample. In some embodiments, the method includes steps of separating the marker bound cells from the non-bound materials in the biological sample.

In some embodiments, the marker conjugated to the recombinant Y3 protein is a marker that emits a signal that can be detected in the biological sample without prior separation of marker bound material from non-bound material in the biological sample.

In further preferred embodiments, the subject invention provides methods of preventing a disease caused by microbes or viruses, the method comprising detecting the presence of microbes or viruses that can cause disease in a subject using the methods of the subject invention and administering to the subject in which the presence of the microbes or viruses were detected a composition of the subject invention, wherein the composition comprises recombinant Y3 proteins either conjugated to a therapeutic moiety or unconjugated.

In other preferred embodiments, the subject invention provides methods of preventing a cancer disease, the method comprising detecting the presence of cancer cells in a subject using the methods of the subject invention and administering to the subject in which the presence of cancer cells was detected a composition of the subject invention, wherein the composition comprises recombinant Y3 proteins either conjugated to a therapeutic moiety or unconjugated.

In further preferred embodiments, the subject invention provides methods of treating a disease caused by microbes or viruses, the method comprising detecting the presence of microbes or viruses that can cause disease in a subject using the methods of the subject invention and administering to the subject that suffers from a disease caused by the presence of the microbes or viruses a composition of the subject invention, wherein the composition comprises recombinant Y3 proteins either conjugated to a therapeutic moiety or unconjugated.

In other preferred embodiments, the subject invention provides methods of treating a cancer disease, the method comprising detecting the presence of cancer cells in a subject using the methods of the subject invention and administering to the subject that suffers from a cancer disease a composition of the subject invention, wherein the composition comprises recombinant Y3 proteins either conjugated to a therapeutic moiety or unconjugated.

The terms "treatment", "treating", "treat" or equivalents of these terms refer to healing, alleviating, relieving, altering, remedying, ameliorating, improving, or affecting the condition or the symptoms of a subject suffering from a disease, for example, a disease caused by a microbe, a virus or a cancer disease. When provided therapeutically, the composition of the subject invention is provided at (or shortly after) the onset of a symptom. The therapeutic administration of the composition serves to attenuate any actual symptoms.

The terms "preventing", "preventive", "prophylactic" or equivalents of these terms indicate that the composition of the subject invention is provided in advance of any disease symptoms and are a separate aspect of the invention (i.e., an aspect of the invention that is distinct from aspects related to the terms "treatment", "treating", "treat" or equivalents of these terms which refer to healing, alleviating, relieving, altering, remedying, ameliorating, improving, or affecting the condition or the symptoms of a subject suffering with an inflammatory disease, for example, a gastrointestinal disorder). The prophylactic administration of the composition of the subject invention serves to prevent or attenuate any subsequent symptoms or disease.

The subject to be treated can be suffering from or be at risk of developing the disorder, for example, a disease caused by a microbe, a virus or a cancer disease. In methods of the subject invention, a disease is prevented when a disease causing microbe, virus or cancer cell is detected in the subject or a biological sample from the subject but the subject is not yet suffering from clinically overt diseases symptoms. In methods of the subject invention, a disease is treated when a disease causing microbe, virus or cancer cell is detected in the subject or a biological sample from the subject and the subject is suffering from clinically overt diseases symptoms.

Disease caused by microbes and diagnosed, prevented and/or treated by methods of the subject invention include, but are not limited to, parasitic diseases, including, but not limited to, haemonchosis, schistosomiasis, and trichinellosis. Microbes to be treated include, but are not limited to, *Haemonchus contortus, Schistosoma mansoni, Trichobilharzia ocellata*, and *Trichinella spiralis*.

Cancer diseases diagnosed, prevented and/or treated by methods of the subject invention include breast cancer, ovarian cancer, uterus cancer and T cell leukemia.

The term "sample" refers to a biological sample obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred samples include, but are not limited to, blood, serum, plasma, urine, stool, saliva, cerebrospinal fluid, amniotic fluid, seminal fluid, intrauterine fluid, cervical fluid, or tissues including, but not limited to, cancer biopsy tissues, mucosal biopsy tissues, endometrial biopsy tissues. In addition, one of skill in the art would realize that some samples would be more readily analyzed following a fractionation or purification procedure, for example, separation of whole blood into serum or plasma components.

In some embodiments, methods for assessing and treating infertility are provided, the methods comprising obtaining a biological sample originating from the reproductive tract of a female and/or a male, contacting the biological sample with a composition of the subject invention, which composition comprises a recombinant Y3 protein conjugated to a detectable marker prepared according to the subject invention and wherein the interaction of the recombinant Y3 protein with cells in the biological sample is detected by the presence of the marker in the biological sample. In some embodiments, the method includes steps of separating the marker bound cells from the non-bound materials in the biological sample.

Without wanting to be bound by theory, it is believed that the effectiveness of compositions of the subject invention can be explained by the binding of recombinant Y3 protein to glycans expressed on microbes, viruses and cancer cells, specifically by binding of the recombinant Y3 protein to GalNAcβ1-4(Fucα1-3)GlcNAc (LDNF) or glycans carrying this moiety present on certain microbes, viruses and cancer cells.

Further provided are methods for screening for compounds useful in the diagnosis, prevention and/or treatment of diseases caused by microbes, viruses, cancer diseases and infertility. The method is based on the LDNF-binding pocket provided by the subject invention, which LDNF-binding pocket can be used to identify compounds, small molecular drugs, antibodies, aptamers and other molecules that efficiently and specifically bind to LDNF or glycans carrying this moiety.

In methods provided by the subject invention, which methods prevent and/or treat cancer diseases, the compositions comprising recombinant Y3 protein bind to and induce apoptosis in cells of the cancer. The recombinant Y3 protein has the surprising and advantageous properties of binding specifically and efficiently to LDNF or glycans carrying this moiety on cancer cells and inducing apoptosis in the cancer cells.

Further advantageously, the recombinant Y3 proteins bind to and kill microbes and viruses. Without wanting to be bound by theory, it is believed that the effectiveness of compositions of the subject invention in killing microbes and viruses can also be explained by the binding of recombinant Y3 protein to LDNF or glycans carrying this moiety on the surface of microbes and viruses.

In certain embodiments, methods are provided for screening for novel glycan antigens that specifically interact with Y3 protein. Also provided are screening methods to identify and characterize Y3 homologs in other fungal species and to develop a new glycan binding protein scaffold based on the Y3-LDNF binding pocket provided by the subject invention for biomedical and research applications.

Advantageously, the LDNF-binding pocket of Y3 can be used to screen and select other Y3 homologues for efficient and specific binding to LDNF or glycans carrying this moiety and use in the methods of the subject invention. The skilled artisan is readily able to design molecules based on Y3 homologues which molecules can interact with LDNF similar to Y3 based upon the Y3 LDNF-binding pocket and identification of residues critical for the LDNF-Y3 interaction as provided herein. Using methods of the subject invention, the binding residues in Y3 critical for the interaction with LDNF were identified to be D26 and N122. Based on the disclosures made herein, the skilled artisan is readily able to design mutants and small molecules that mimic the Y3-LDNF interaction disclosed herein for use with methods of the subject invention.

In some embodiments, the subject invention provides methods for assessing and/or treating infertility. In specific embodiments, the compositions of the subject invention comprise recombinant Y3 protein that binds to and inhibits LDNF-containing glycodelins present in the reproductive tract. Without wanting to be bound by theory, it is believed that the effectiveness of compositions of the subject invention can be explained by the binding of recombinant Y3 protein to LDNF on glycodelins present in the reproductive tract, which glycodelins are involved in inhibition of the interaction between sperm and egg cell.

In further embodiments, the methods for assessing the presence of glycodelins in a subject comprise obtaining a biological sample originating from the reproductive tract of a female and/or male subject suspected of suffering from infertility, contacting the biological sample with a composition of the subject invention, which composition comprises a recombinant Y3 protein conjugated to a detectable marker prepared according to the subject invention and wherein the interaction of the recombinant Y3 protein with the cancer cells in the biological sample of the subject is detected by the presence of the marker in the biological sample. In some embodiments, the method includes steps of separating the marker bound cells from the non-bound materials in the biological sample.

In other preferred embodiments, the subject invention provides methods of treating infertility, the method comprising detecting the presence of glycodelins in a subject using the methods of the subject invention and administering to the subject that suffers from infertility a composition of the subject invention, wherein the composition comprises recombinant Y3 proteins.

Further provided are methods for expressing a recombinant Y3 protein in a subject, the method comprising introducing into the subject a nucleic acid encoding a recombinant Y3 operably linked to a promoter sequence for cell-type specific expression of the recombinant Y3 protein in cells of the subject.

The subject invention also provides kits for diagnosis of cancer comprising an agent that detects one or more glycans expressed on the surface of the cells of said cancer. Agents that are capable of detecting a glycan in the biological sample of a subject are those that interact with or bind a glycan moiety present on a polypeptide or a lipid. In preferred kits of the subject invention the glycan bound by the compositions of the invention are LDNF-related glycans.

Further provided are nucleic acids encoding a recombinant Y3 protein, which nucleic acids comprise a codon-optimized sequence encoding the recombinant Y3 protein suitable for expression of the recombinant Y3 protein in an expression system of the invention including, but not limited to, an expression system based on yeast as provided herein. The method of codon-optimization for efficient expression of a polypeptide using a selected expression system is within the purview of a person with ordinary skill in the art.

The term "protein" as used herein is understood as denoting peptide or polypeptides which comprise two or more amino acids bonded via peptide bonds.

In some embodiments, the subject invention provides recombinant Y3 fusion proteins. The term "fusion protein" or "fusion polypeptide" refers to a protein or polypeptide which is constituted from sequences taken from more than one other protein or polypeptide, joined contiguously so that the sequences are expression as a single protein or polypeptide.

The term "polypeptide" encompasses native or artificial proteins, protein fragments and polypeptide analogs of a protein sequence. A polypeptide may be monomeric or polymeric. The term "isolated polypeptide" is a polypeptide that by virtue of its origin or source of derivation (1) is not associated with naturally associated components that accompany it in its native state, (2) is substantially free of other proteins from the same species, (3) is expressed by a cell of a species different from where the protein naturally originates, or (4) does not occur in nature. A polypeptide that is chemically synthesized or synthesized in a cellular system different from the cell from which it naturally originates is also considered "isolated" from its naturally associated components. A polypeptide can also be rendered substantially free of naturally associated components by isolation, using purification techniques well known in the art.

The terms "specifically binds," "specificity," "specifically reacts," or "specifically interacts," as used herein, refers to the ability of a recombinant Y3 protein to detectably bind an epitope presented on an antigen, such as epitopes of GalNAcβ1-4(Fucα1-3)GlcNAc, i.e. fucolysated LacdiNAc (LDNF) glycan, while having relatively little detectable reactivity with other glycan moieties or proteins. Specificity can be relatively determined by binding or competitive assays, using e.g., Biacore instruments. Specificity can be exhibited by, e.g., an about 10:1, about 20:1, about 50:1, about 100:1, about 10,000:1 or greater ratio of affinity/avidity in binding to the specific antigen versus nonspecific binding to other irrelevant molecules.

The term "nucleic acid" as used herein refers to a deoxy-ribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides.

As used herein, a vector is a DNA sequence having the elements necessary for the transcription/translation of a gene. Such elements would include, for example, promoters. Various classes of promoters, including promoters that drive expression specifically in intestinal cells, are well known in the art and can be obtained commercially or assembled from the sequences and methods, which are also well known in the art. A number of vectors are available for expression and/or cloning, and include, but are not limited to, pBR322, pUC series, M13 series, and pBLUESCRIPT vectors (Stratagene, La Jolla, CA).

As used herein, the term "expression construct" refers to a combination of nucleic acid sequences that provides for transcription of an operably linked nucleic acid sequence where operably linked components are in contiguous relation.

The term "subject", as used herein, describes an organism, including mammals such as primates, to which treatment with the compositions according to the subject invention can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters. The subject invention provides methods having both human and veterinary utility. Non-human mammalian species which benefit from the disclosed methods include, and are not limited to, apes, chimpanzees, orangutans, monkeys; domesticated animals (pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, giant pandas, hyena, seals, sea lions, and elephant seals.

The term "effective amount", as used herein, refers to an amount that is capable of treating or ameliorating a disease or condition or otherwise capable of producing an intended therapeutic effect. In preferred embodiments, an effective amount is an amount that is useful for preventing and/or treating a disease caused by a microbe, virus or a cancer disease or infertility.

The quantity to be administered, both according to number of treatments and unit dose, depends on the disease to be treated, the subject to be treated, the state of the subject and the protection desired. Precise amounts of the therapeutic composition also depend on the judgment of the practitioner and are peculiar to each individual. Generally, the dosage of the composition of the subject invention will vary depending upon such factors as the patient's age, weight, height, sex, general medical condition and previous medical history.

In some embodiments of the subject invention, the method comprises administration of multiple doses of the composition. The method may comprise administration of 1, 2, 3, 4, 5, 6, 7, 8, 9, 10, 15, 20, 25, 30, 35, 40, or more therapeutically effective doses of a composition comprising the recombinant Y3 protein as described herein. In some embodiments, doses are administered over the course of 1 day, 2 days, 3 days, 4 days, 5 days, 6 days, 7 days, 10 days, 14 days, 21 days, 30 days, or more than 30 days.

The frequency and duration of administration of multiple doses of the compositions of the subject invention is such as to prevent and/or treat an infection with a microbe or a virus, prevent and/or treat the proliferation of cancer cells and/or prevent and/or treat infertility.

Moreover, treatment of a subject with a therapeutically effective amount of the recombinant Y3 protein of the invention can include a single treatment or can include a series of treatments. It will also be appreciated that the effective dosage of a composition of the subject invention used for treatment may increase or decrease over the course of a particular treatment. Changes in dosage may result and become apparent from the results of diagnostic assays for detecting markers of a disease caused by a microbe or a virus or markers of a cancer disease known in the art and described herein or detection of successful sperm-egg cell interaction.

The composition of the subject invention can comprise a pharmaceutically acceptable carrier and/or excipient comprising substances, such as an inert vehicle, or pharmaceutical acceptable adjuvants, and can contain preservatives and additives usual for injection solutions, such as stabilizing agents, salts or saline, and/or buffers etc. Examples pharmaceutically acceptable substances are well known to a person of ordinary skill in the art and such embodiments are within the purview of the current invention.

The pharmaceutical composition may be a liquid formulation or a solid formulation. When the pharmaceutical composition is a solid formulation it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip or a film. When the pharmaceutical composition is a liquid formulation it may be formulated as an oral solution, a suspension, an emulsion or syrup. Said composition may further comprise a carrier material independently selected from, but not limited to, the group consisting of lactic acid fermented foods, fermented dairy products, resistant starch, dietary fibers, carbohydrates, proteins, and glycosylated proteins.

Pharmaceutical compositions, as disclosed herein, can be formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. Pharmaceutical composition according to the invention may also be formulated to release active agents substantially immediately upon administration or at any predetermined time or time period after administration.

Exemplary modes of administration include oral, rectal, transmucosal, topical, transcervical, transuterine, transurethral, transdermal, inhalation, parenteral (e.g., intravenous, subcutaneous, intradermal, intramuscular, and intraarticular) administration. Injectables can be prepared in conventional forms, either as liquid solutions or suspensions, solid forms suitable for solution or suspension in liquid prior to injection, or as emulsions. Alternatively, one may administer the composition of the subject invention in a local rather than systemic manner, for example, in a depot or sustained-release formulation.

Pharmaceutical composition can also be formulated as a food composition, a dietary supplement, a functional food, a medical food or a nutritional product as long as the required effect is achieved, e.g. diagnosis, treatment and/or prevention of a disease caused by microbes, viruses and/or cancer cells present in the intestinal tract. Said food composition may be chosen from the group consisting of beverages, yogurts, juices, ice creams, breads, biscuits, crackers, cereals, health bars, spreads and nutritional products or animal foods. The food composition may further comprise a carrier material, wherein said carrier material is chosen from the group consisting of lactic acid fermented foods, fermented dairy products, resistant starch, dietary fibers, carbohydrates, proteins and glycosylated proteins.

For oral administration, the composition of the subject invention can be formulated into conventional oral dosage forms such as tablets, capsules, powders, granules and liquid preparations such as syrups, elixirs, and concentrated drops. Non-toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials are also necessary. For example, starch, gelatin, sugars such as lactose or dextrose, and natural or synthetic gums can be used as binders. Disintegrants are also necessary in the tablets to facilitate break-up of the tablet. Disintegrants include starches, clays, celluloses, algins, gums and cross-linked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

Vectors useful in the subject invention can include, for example, nucleic acid vectors, such as naked DNA and plasmids, and viral vectors, such as retroviral vectors, parvovirus-based vectors (e.g., adenoviral-based vectors and adeno-associated virus (AAV)-based vectors), lentiviral vectors (e.g., Herpes simplex (HSV)-based vectors), and hybrid or chimeric viral vectors, such as an adenoviral backbone with lentiviral components (see, e.g., Zheng et al., Nat. Biotech., 18(2), 176-80 (2000); International Patent Application WO 98/22143; International Patent Application WO 98/46778; and International Patent Application WO 00/17376) and an adenoviral backbone with AAV components (see, e.g., Fisher et al., Hum. Gene Ther., 7, 2079-2087 (1996)), all of which are hereby incorporated by reference). Vectors and vector construction are known in the art (see, e.g., Sambrook et al., Molecular Cloning: A Laboratory Manual, 2d edition, Cold Spring Harbor Laboratory, N Y (1989); and Ausubel et al., Current Protocols in Molecular Biology, Green Publishing Associates and John Wiley & Sons, New York, N.Y. (1994), both of which are hereby incorporated by reference).

The vector can contain any suitable promoter and other regulatory sequences (e.g., transcription and translation initiation and termination codons, which are specific to the type of host) to control the expression of the nucleic acid sequence encoding the polypeptide in the expression system used. The promoter can be a native or nonnative promoter operably linked to the nucleic acid molecule described above. The selection of promoters, including various constitutive and regulated promoters, is within the skill of an ordinary artisan.

Examples of regulated promoters include inducible, repressible, and tissue-specific promoters. Specific examples include tetracycline-regulated promoters, steroid-regulated promoters, theophylline riboswitch, viral promoters, such as adenoviral promoters, cytomegalovirus promoters and AAV promoters. Additionally, combining the nucleic acid described above with a promoter is within the skill in the art.

Cells (e.g., isolated host cells) containing the above-described polypeptide or nucleic acid molecule encoding the polypeptide, optionally in the form of a vector, are also provided by the disclosure. Preferred cells are yeast including, but not limited to, *Saccharomyces, Pichia, Kluyveromyces, Hansenula*, Arxula adeninivorans, and *Yarrowia*.

Other host cells useful in the subject invention include *E. coli* (e.g., *E. coli* Tb-1, TG-2, DH5a, XL-Blue MRF' (Stratagene), SA2821, and Y1090), *Bacillus subtilis, Salmonella typhimurium, Serratia marcescens, Pseudomonas* (e.g., *P. aerugenosa*), *N. grassa*, insect cells (e.g., Sf9, Ea4), and cells derived from a mammal, including human cell lines. Specific examples of suitable eukaryotic host cells include SKOV-3, SKBR3, MDA453, MCF-7, VERO, HeLa, 3T3, Chinese hamster ovary (CHO) cells, W138 BHK, COS-7, and MDCK cells. Alternatively, cells from a mammal, such as a human, to be treated in accordance with the methods described herein can be used as host cells.

Methods of introducing vectors into isolated host cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., Molecular Biology: A Laboratory Manual, Cold Spring Harbor Laboratory, N Y (1989); Davis et al., Basic Methods in Molecular Biology (1986); and Neumann et al., EMBO J. 1, 841 (1982), all of which are hereby incorporated by reference). In one embodiment, the cell containing the vector or nucleic acid molecule is transcribed and translated efficiently by the cell.

The therapeutic compositions of the subject invention can conventionally be administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The pharmaceutical composition of the subject invention can also include sustained-release preparations, such as semipermeable matrices of solid hydrophobic polymers containing the polypeptide, which matrices are in the form of shaped articles (e.g., films, liposomes, or microparticles). It will be apparent to those persons skilled in the art that certain carriers may be more preferable depending upon, for instance, the route of administration and the concentration of composition being administered.

Parental administration of compositions of the subject invention can involve the preparation of a slow-release or sustained-release system, such that a constant dosage is maintained (see, e.g., U.S. Pat. No. 3,610,795, which is hereby incorporated by reference). Preparations for parenteral administration include sterile aqueous or nonaqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases and the like.

The exact amount of the compositions required to treat a disease caused by microbes, viruses, a cancer disease or infertility may vary, depending on the species, age, gender, weight, and general conditions of the mammal, the particular polypeptide, nucleic acid, vector, or cell used, the route of administration, and whether other drugs are included in the regimen. Thus, it is not possible to specify an exact amount for every composition. However, an appropriate, suitable amount can be determined by one of ordinary skill in the art using only routine experimentation given the teachings herein. The dosage ranges for the administration of the compositions are those large enough to produce the desired effect; however, the dosage should not be so large as to cause adverse side effects, such as unwanted cross-reactions, ana-phylactic reactions, and the like. Dosage can vary, and can be administered in one or more (e.g., two or more, three or more, four or more, or five or more) doses daily, for one or more days (or any suitable period of time to advance treatment). The composition can be administered immedi-ately upon determination of a disease caused by a microbe or virus, a cancer disease or infertility and continuously or intermittently administered.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

All patents, patent applications, provisional applications, and publications referred to or cited herein are incorporated by reference in their entirety, including all figures and tables, to the extent they are not inconsistent with the explicit teachings of this specification.

It should be understood that the examples and embodi-ments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof dis-closed herein can be combined with any and/or all other elements or limitations (individually or in any combination) or any other invention or embodiment thereof disclosed herein, and all such combinations are contemplated with the scope of the invention without limitation thereto.

Materials and Methods

Disclosed herein is the detailed biochemical, functional, and structural characterization of the fungal small protein Y3. The biochemical studies of recombinant mature Y3 produced in a yeast expression system validated its anti-tobamovirus activity and revealed its glycan binding capa-bility. Given the significance of glycans to cancer develop-ment and apoptosis (4-6), it was further demonstrated that Y3 selectively and potently induced caspase-dependent apoptosis of human T-cell leukemia Jurkat cells. Glycan array screening identified a novel glycan antigen that Y3 showed strong specific interactions with. Finally, a high-resolution crystal structure of Y3 was determined and it was discovered that Y3 contains a unique GBP tertiary structure. The Y3 glycan binding pocket was characterized.

Molecular Cloning, Protein Expression and Purification.

A codon-optimized gene encoding the full length Y3 was synthesized (Eurofins Genomics, USA). A construct with the signal peptide removed (SP-free) was amplified via PCR (primers illustrated in Table 1).

TABLE 1

| Primers used in this work | |
|---|---|
| Primer name | Sequence |
| Y3FXh | 5'-GTATCTCTCGAGAAAAGACAAGATCCTTTG-3' (SEQ ID NO: 4) |
| Y3RNt | 5'-TTTTCCTTTTGCGGCCGCTTAAAAATCAGTGG-3' (SEQ ID NO: 5) |
| D26AFw | 5'-TGCTATGCCAACTTTGGGAATCGTGATGTTGCAGCA-3' (SEQ ID NO: 6) |
| D26ARv | 5'-TGCTGCAACATCACGATTCCCAAAGTTGGCATAGCA-3' (SEQ ID NO: 7) |
| N122AFw | 5'-GATCCGGCTGATGGAGACTGTTCCACTGATTTTTAA-3' (SEQ ID NO: 8) |
| N122ARv | 5'-TTAAAAATCAGTGGAACAGTCTCCATCAGCCGGATC-3' (SEQ ID NO: 9) |

Both genes were cloned into the pPICZαA vector (Thermo Fisher Scientific) (62). The pPICZαA-Y3 construct was used as the template to create Y3 mutants, by site-directed mutagenesis PCR with prim-ers shown in Table 1. Plasmids were transformed into *Pichia pastoris* X-33 following manufacturer's instruc-tions (Thermo Fisher Scientific). After selection, mul-tiple single colonies were randomly picked to assess the Y3 production in 10 mL culture. The culture with the highest yield (10 mL) was inoculated into 1 L of YPD (1% yeast extract, 2% peptone, and 2% glucose) to produce Y3 following our previous protocol (63). After three days, the culture supernatant was harvested by centrifugation, filtered and dialyzed twice against 1 L of PBS buffer. The supernatant was further concen-trated, and purified by gel filtration chromatography (HiLoad 16/60 SuperDex-75 column, AKTA FPLC System, GE Healthcare) with 150 mM NaCl, and 20 mM Tris-HCl, pH 7.5. Purified Y3 was concentrated to 10 mg·mL$^{-1}$ as determined by Bradford assay (BSA as standard) and the purity of Y3 was determined by SDS-PAGE.

Ellman's Test for Free Thiol Determination.

Standard Ellman's test was used to detect the free thiol groups in purified Y3 protein. Ten microliter Y3 (100 μM) or L-cysteine (100 μM) was mixed with 990 μL DTNB reagent (100 μM, Thermo Fisher Scientific) and incubated at room temperature for 5 min. The optical absorbance at 412 nm was measured and recorded.

Quantitation of Carbohydrate Content in Y3.

Recombinant Y3 was processed with the phenol-sulfuric acid method for total carbohydrate determination (43, 44). Protein stock solutions (0.2 to 10 μL at 10 mg/mL) were diluted to 400 μL with water and mixed with 10 μL of 80% w/w phenol. Concentrated sulphuric acid (1.0 mL) was quickly added into the mixture. After incubating on ice for 10 min, the mixture was then incubated in water bath at 25° C. for 10 min. Protein free buffer and D-Glu were used as controls. Absorbance was recorded at 490 nm.

Anti-Tobamovirus Assay.

Purified Tobacco mild green mosaic virus (TMGMV) (Virgaviridae, Tobamovirus, formerly known as Tobacco mosaic virus strain U2) (GenBank Acc. No. EF469769) (26.5 mg/ml) was obtained from R. Charudattan (BioPro-dex, Inc.) (64). The ability of recombinant Y3 to inhibit TMGMV infection was evaluated using a range of protein concentrations (0.078, 0.15, 0.31, 0.625, 1.25, 2.5 μM) mixed with a constant concentration of TMGMV (26.5 μg/ml). Leaves (3rd, 4th and 5th leaves from the apex) were detached from approximately 60 8-week old plants of *Nicotiana glutinosa*. Leaves were combined in a bag and then randomly selected for each inoculation. Recombinant Y3 and purified TMGMV were defrosted on ice, diluted with water, mixed to form the final concentrations, and kept on ice until inoculation. Treatments were inoculated in order of Y3 dilution from the most concentrated to the least. The left half of each leaf was inoculated with 50 μl of recombinant Y3 plus TMGMV, and the right half with an equal concentration of TMGMV only. Inoculated leaves were placed in a moist chamber in the dark for 48 h after which time the number of local lesions per each leaf half were recorded. All experiments were repeated 6 times. The percent inhibition was calculated as followed: 1–(No. of local lesions Y3+TMGMV/No. of local lesions from TMGMV alone)× 100%.

To examine the effects of time and temperature on the ability of recombinant Y3 to interfere with TMGMV infectivity, a mixture containing recombinant Y3 and purified TMGMV (0.078 μM and 26.5 μg/ml, respectively) were maintained either on ice or at room temperature for 0 min and 20 min before inoculation to the left half of leaves. Purified TMGMV (50 μl of 26.5 μg/ml solution) was inoculated to the right half of leaves 0 and 20 min after incubation. Six leaves were tested per treatment. The percent inhibition was calculated as followed: 1–(No. of local lesions Y3+TMGMV/No. of local lesions from TMGMV alone)× 100%.

Annexin V/7-AAD Staining to Quantitate Cells in Early and Late Apoptosis Stages.

Apoptosis in Jurkat cells was induced with WT Y3 (0, 0.025, 0.1, 0.25, 1 μM) along with two Y3 mutants Y3D26A (1 μM) and Y3N122A (1 μM) for 4 h or 20 h. Cells were then stained with Annexin V-APC and 7-aminoactinomycin D (7-AAD) to evaluate early and late apoptosis by flow cytometry according to manufacturer's protocol (Biolegend). Briefly, 106 cells were washed twice with PBS and stained with 5 μL of Annexin-APC (5 μg·ml$^{-1}$) and 10 μL of 7-AAD (2.5 μg·mL$^{-1}$). After incubation at room temperature for 15 min in the dark, 400 μL of binding buffer was added to each sample. Flow cytometric analysis was carried out using a FACS Fortessa (BD Bioscience) and cells at early and late apoptosis stages were identified using FlowJo program. The total apoptotic cells referred to the combination of early and late ones. Three independent experiments were performed for each set.

Cell imaging with FITC-Y3.

Y3 was labeled with fluorescein by reacting the purified protein with NHS-fluorescein (Fisher Scientific). Jurkat and HEK293 (control) cells were incubated with Y3-FITC (1 μM) for 1 h, then washed with PBS. Y3-FITC has an absorption maximum at 495 nm and emission maximum at 525 nm. A Zeiss Fluorescent microscope AXIO, AXioCam MRm camera, and AxioVision Rel 4.8.1 software was used to capture imaging pictures.

Western Blot Analysis of Caspase-Dependent Apoptosis.

Jurkat cells were treated with Y3 (0.01 μM, 0.1 μM, 1 μM) or Y3 (1 μM) plus the pan-caspase inhibitor Z-VAD-FMK (20 μM) for 20 h. Cells were then collected and washed twice with PBS. An equal amount of protein from the cell lysate of each sample was analyzed by 12% SDS-PAGE. After electrophoresis, proteins were transferred to PVDF membranes, blocked for 1 h with 5% fat-free milk at room temperature, and blotted with the indicated primary antibodies (anti-cleaved caspase-3, 1:1000; anti-caspase-8, 1:1000; anti-cleaved caspase-9, 1:1000, anti-β-actin, 1:1000, Cell Signaling Technology) with gentle agitation at 4° C. overnight. Following a wash step with Tris-buffered saline/Tween-20, the membranes were incubated with HRP-conjugated secondary antibodies at room temperature for 1 h and the immune complexes were detected using the standard electrochemiluminescence method.

Hemagglutination Assays.

Agglutinating activity of Y3 was examined by using human red blood cells, type 0+ and rabbit red blood cells (Innovative research, USA). A serial twofold dilution of the Y3 solution (2 μM starting concentration) in microtiter U-plates (50 μL) was mixed with 50 μL of 2% suspension of red blood cells in PBS at room temperature. The results were recorded when the blank was fully sedimented. Experiments were repeated multiple times.

Determination of the Carbohydrate Binding to Y3.

D-Glu, α-D-mannose, β-D-galactose and lactose were tested with isothermal titration calorimetry (ITC). Purified Y3 was diluted to 100 μM and dialysed against 150 mM NaCl and 20 mM Tris-HCl, pH 7.5 for 16 h. Protein (200 μL) was then placed into a MicroCal iTC200 (Malvern) reaction cell, while different carbohydrates in the same buffer at a concentration of 1-5 mM were injected into the reaction cell over time at 25° C. Raw data were integrated, normalized and evaluated using ORIGIN 7.0 according to the one-site binding model. Octet RED384 (ForteBio) was used to determine the binding of D-galactose 6-sulfate, N-acetyl-D-galactosamine and D-galactosamine to biotinylated Y3 in black 96 wells plates (Nunc™ F96 MicroWell™ plate, Thermo Scientific) following a previous protocol (65). All experiments were performed in triplicate. Data were processed to calculate kinetic and affinity parameters using the ForteBio software.

Glycan Microarray Analysis of Y3's Glycan Binding Profile.

Glycan microarray analysis was performed by the Consortium for Functional Glycomics (Core H). The Mammalian Printed Array, version 5.3, consists of 600 glycans in replicates of six and was used in this work. For screening the array, Y3 was biotinylated using EZ-Link NHS-PEG4-Biotinylation Kit (Thermo Scientific) according to manufacturer's instructions. Biotin-labeled Y3 at 5 μg/mL and 50 μg/mL were analyzed as previously described (61). Streptavidin-488 was used to detect biotinylated Y3 that bound to the glycans on the array. The average binding for each glycan target as well as standard deviation (SD) was calculated after the highest and lowest point from each set of six replicates were removed, and glycans were then ranked and sorted. The scanner response was linear to a maximal RFU value of about 50,000.

Crystallization of Y3.

Initial Y3 crystallization was carried in a vapor diffusion sitting drop format with a homemade matrix screen designed for glycoproteins (CrystalQuick 96 well, Hampton Research). Small plate clusters of Y3 crystals were identified in a condition containing 20% PEG-4000 and 0.1 M CHES, pH 10.5 in 15 min at 25° C. Optimization of precipitant and pH, along with microseeding were performed in a hanging drop format (24 well VDX crystallization plate, Hampton Research). Protein (1.8 μL, 10 mg·mL-1) plus 2.0 μL of precipitant were balanced against 1 mL of reservoir solution. The resultant plate-shaped single crystals with a size of ~20×20×100 μm were obtained in a final condition that contained 16% PEG-4000, 10% v/v glycerol and 0.1 M CHES, pH 9.5 in 48 h. Crystals of suitable size were harvested and flash frozen in liquid nitrogen with an additional 10% glycerol as cryoprotectant. Heavy atoms derivative crystals for single wavelength derivative (SAD) were obtained through co-crystallization or soaking. Compounds (Heavy Atom Screen Kits, Hampton Research) containing derivative elements (Pt, Au, Hg, I) were selected according to their solubility (pH 9.5-10.5).

Diffraction Data Collection and Processing.

Y3 native and derivative crystal X-ray diffraction data sets were collected on beamlines 21-ID-G and 21-ID-F of the Life Sciences Collaborative Access Team (LS-CAT) facility at the Advanced Photon Source (APS), Argonne National Laboratory (ANL) with a wavelength of 0.9786 Å at 100 K.

Data sets were merged using XDS program package (66) and then scaled with AIMLESS from the CCP4 suite (67) to space group P21, in two diverse forms with different unit cell parameters. Y3 native crystals diffract X-ray to 1.18 Å, while the Pt-derivative data set was truncated at 1.70 Å resolution. Native data sets had large non-origin Patterson peaks as indicated by PHENIX.XTRIAGE from PHENIX suite, suggesting the presence of translational noncrystallographic symmetry (tNCS).

Atomic Structure Determination and Refinement.

The structure of Y3 was determined with Pt-SAD. The number and location of heavy atoms were identified with SHELXD. Initial phase calculation was carried using SHELXE (68) and further refined with MLPHARE, PIRATE (8) and PHASER (70). An interpretable 69electron-density map was generated with SOLOMON with 20% solvent flattering (71). The model building was initiated with SHELXE, and completed using BUCCANEER (72), ARP/wARP (73) and COOT (74). Final coordinates were refined with REFMAC5 (75) and PHENIX.REFINE (76). Carbohydrates and CHES from the crystallization conditions were added manually with COOT upon careful inspection of the electron-density maps. Derivative ions were added manually into the calculated anomalous difference map, with their occupancy and anisotropic B-factors refined sequentially. The quality of the models was evaluated using a sigma-weighted, simulated annealing composite omit map. Structural illustrations were prepared with PyMOL. Statistics on data collection and atomic structure refinement were given in Table 1. The refined coordinates have been deposited in the PDB (accession codes 5V6I and 5V6J).

Docking of LDNF into Y3 Binding Pocket.

Docking was conducted using AutoDock 4.2 (77). LDNF was constructed and energy minimized with Spartan '08 (78). Standard algorithms and docking procedures were used for a rigid protein and a flexible ligand in a grid covering the entire protein dimer. The hydrogen bonding/π-π interactions and corresponding estimated free energy of ligand binding (AG) were analysed with AutoDockTools 1.5.6. The best docking pose was selected and illustrated.

Mass Spectrometry Analysis of Y3.

For ESI mass spectrometry analysis, protein crystals were picked, washed with the crystallization mother liquor, and dissolved in water. Liquid chromatography (LC) conditions were: 3.0%-60% of 0.1% TFA-acetonitrile in 0.1% TFA-water over 40 min with a flow rate of 1.0 mL·min−1 (ZORBAX SB-C18, Agilent). For MALDI-TOF-MS, sinapic acid was used as matrix (Protea). To determine the potential bound carbohydrates by LC-MS (Agilent), protein samples were treated with peptide N-glycosidase F (PNGase F, New England Biolabs) following manufacturer's protocol.

Screens for Anticancer Activity.

The cells shown in Table 51 were cultured in DMEM medium containing 10% FBS, 100 U·mL−1 penicillin and streptomycin, and maintained at 37° C. in a humidified incubator under 5% CO2. The cells (104 cells in 100 μL), seeded in 96-well plate, were treated with Y3 (10 μM). After incubation at 37° C. for 48 h, a MTT protocol was followed to determine cell viability using a UV/vis microplate spectrophotometer (BioTek). Six replications were performed per treatment and the percent inhibition was calculated as (1−test OD570/non-treated OD570)×100%. Serial concentrations of Y3 (0, 0.25, 0.5, 0.75, and 1 μM) were used to treat Jurkat cells.

Cell Culture.

Jurkat cells were cultured in RPMI-1640 medium containing 10% fetal bovine serum (FBS) and 100 U/mL penicillin/streptomycin at 37° C. in a 5% $CO_2$ incubator.

RNA Extraction, Library Preparation, Sequencing and Analysis.

Jurkat cells were seeded in 6 wells plates ($1\times10^6$ cells per well) and treated with Y3 (1 μM) for 5 h. Jurkat cells without Y3 treatment was used as control. Total RNA was extracted from Jurkat cells using PureLink RNA Mini Kit (Thermo Fisher Scientific), and treated with DNase I (New England Biolabs) to remove genomic DNA. RNA concentration was assessed by a NanoDrop spectrophotometer and RNA integrity was examined by agarose gel. RNA quality and quantity was further analyzed by Beijing Genomics Institute (BGI) prior to RNA-Seq. Library preparation, sequencing and analysis were performed at BGI. Both treatment and control groups were performed with three replicates.

Identification of Differentially Expressed Genes (DEGs).

Fragments per kilobase of transcript per million mapped reads (FPKMs) method was used to calculate gene expression level. Differential expression genes (DEGs) were screened by NOISeq method and transcripts with fold-change values larger than 2 and diverge probability ≥0.8 were determined as DEGs in the analysis.

Gene Ontology Enrichment of DEGs.

Functional enrichment was assessed using the Database for Annotation, Visualization, and Integrated Discovery (DAVID v.6.8) software. The background was set to the default total list of genes expressed in *Homo sapiens*. The statistical significance threshold level for all gene ontology enrichment analyses was set as P-value <0.05.

qRT-PCR.

Total RNA was extracted from cells by using Trizol reagent. Reverse transcription of RNA was performed with the High-Capacity cDNA Reverse Transcription Kit. Real-time PCR in triplicate was performed with SYBR Green Master Mix. The ΔΔct method was used to calculate the relative expression of genes using β-actin RNA as an internal control. The experiments were performed with three replicates.

Statistical Analysis of Experimental Data.

Results were presented as mean±SE of at least three independent experiments. Statistical significance among multiple groups was analyzed by one-way ANOVA followed by Student's t-test for comparison of the results between two groups using Prism 5 (Graphpad Software, Inc). * and ** indicates p<0.05 and p<0.01 statistical differences compared to the control, respectively.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1: Biochemical Characterization of Recombinant Y3

The mushroom *C. comatus* has an annual production of about 0.4 million tons globally and shows a range of bioactivities (e.g., immunomodulation, antimicrobial, and anticancer) (40, 41). In an initial report, Y3 was isolated from the fungal fruiting body and showed anti-TMV activity which was retained after incubating the protein at 90° C. for 10 min (39). A bioinformatic analysis of Y3 predicted an 18-aa signal peptide (SP) at its N-terminus and a potential N-glycosylation site (Asn110) (FIG. 5A) and native Y3 had been reported to be a glycoprotein (39). Considering these putative post-modifications, both full-length and SP-free genes were expressed in *Pichia pastoris* (FIG. 1). To preserve the original structure and activity, no purification-tag was included. Recombinant Y3 was produced only from the SP-free, but not full-length, gene (FIG. 5B-5C). The yield of recombinant Y3 was about 20 mg/L after filtration, concentration and dialysis of the *P. pastoris* culture supernatant. The size-exclusion chromatography analysis of purified Y3 led to a single peak with an estimated molecular weight (MW) of ~39 kDa (FIG. 5B). Denaturing SDS-PAGE analysis revealed a single band of ~12 kDa, similar to that of native Y3 directly isolated from *C. comatus*. Treatment with heat (90° C. for 20 min) or a range of acid/base (pH 3.0-11.5) had no effect on the SDS-PAGE profile of recombinant Y3. The impressive stability of Y3 may be ascribed to the presence of multiple disulfide bridges from its eight cysteine residues (FIG. 5A). Indeed, Ellman's analysis excluded the presence of any free thiol in the recombinant protein (42) (FIG. 2).

Figure 3:
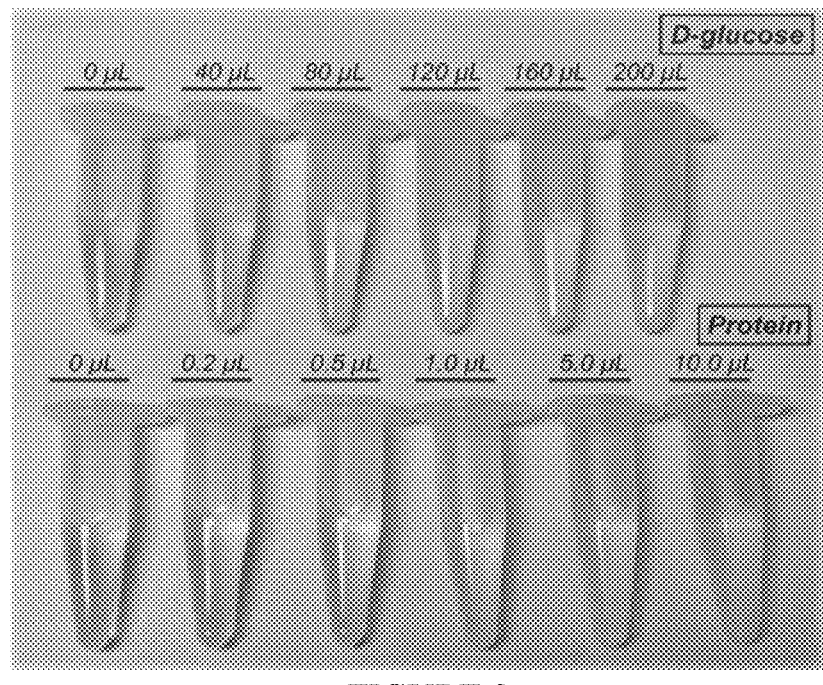
FIG. 3 shows the phenol-sulfuric analysis of the carbohydrate content in purified recombinant Y3.
Figure 4A:
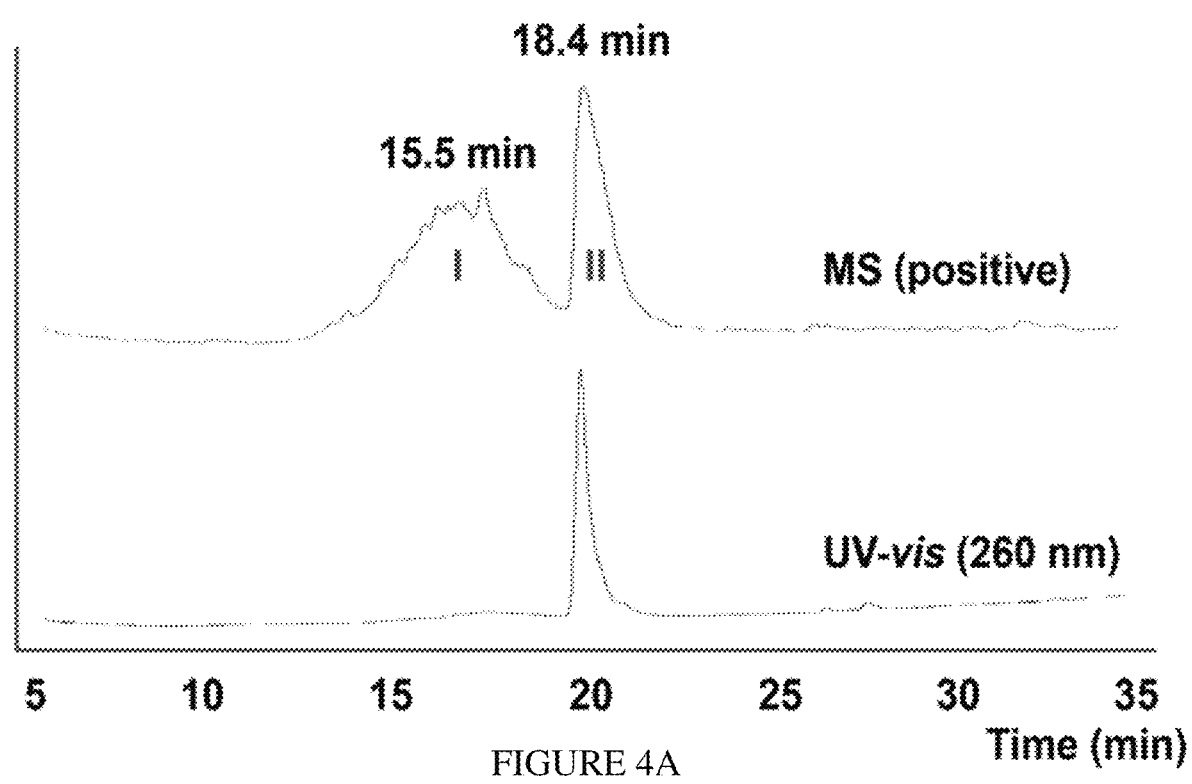
FIG. 4A shows LC and MS traces of recombinant Y3 from a *P. pastoris* expression system.
Figure 4B:
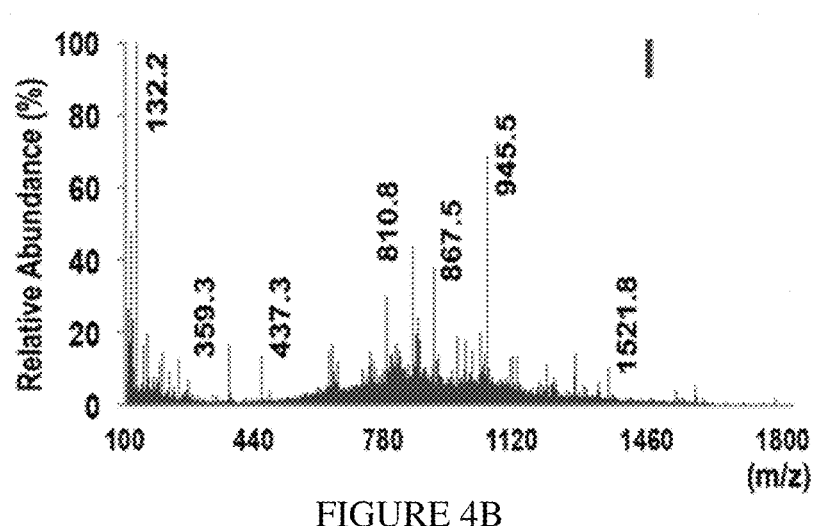
FIG. 4B shows ESI-MA spectrum of peak I.
Figure 4C:
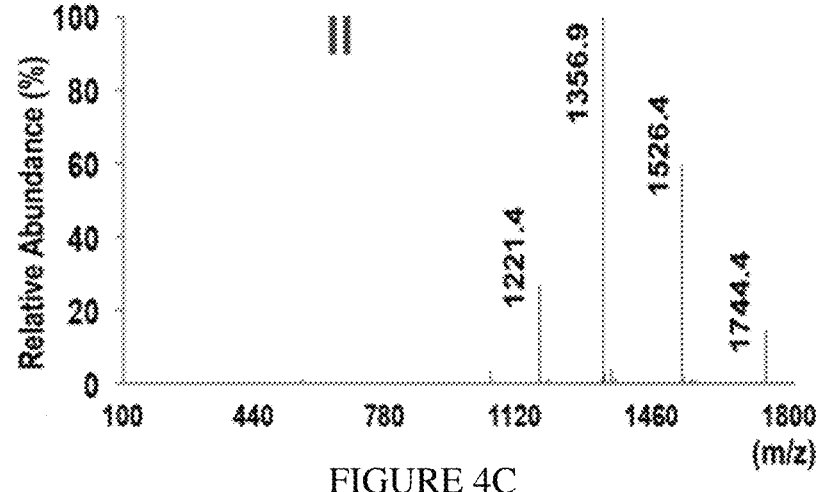
FIG. 4C shows ESI-MS spectrum of peak II.
Figure 5D:
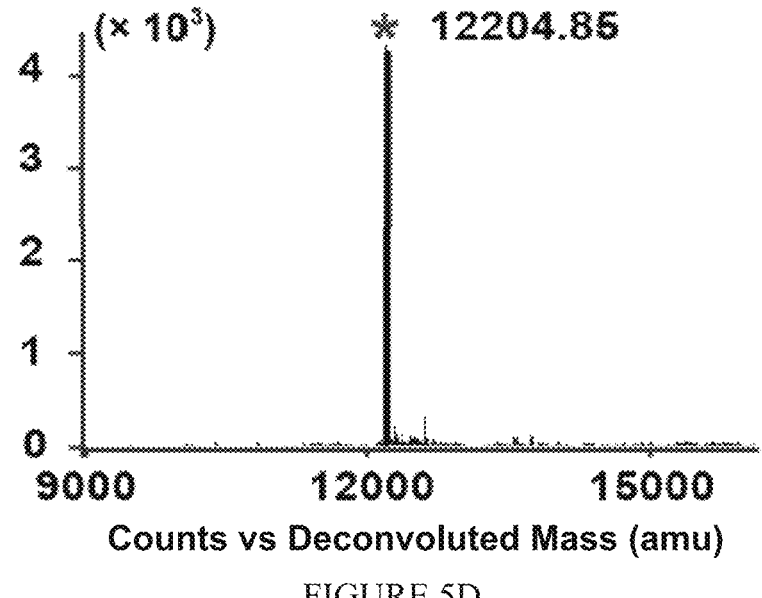
FIG. 5D shows MS analysis of recombinant Y3.

The MW of recombinant Y3 was determined using MALDI-TOF mass spectrometry (MS). The observed MW of 12.20 kDa agreed well with the calculated MW of SP-free Y3 (12.22 kDa) (FIG. 5D). Treatment of the recombinant Y3 with PNGase F, which removes potential N-glycan of glycoproteins, led to no MW change in the MS analysis, suggesting that Y3 is not a glycoprotein. However, carbohydrates were found in the Y3 sample in phenol sulfuric acid analysis, i.e. a 22% of total carbohydrates in the Y3 sample (w/w) (43, 44) (FIG. 3). In light of the above result, a broad peak in the ESI-MS profile that did not possess proteinous UV-vis absorbance at 260 nm was re-examined (FIG. 4A-4C). The peak consisted of a wide range of MWs and likely represented potential carbohydrate fragments bound to Y3. Co-purification of endogenous carbohydrates with recombinant proteins has been uncommonly encountered in previous studies (45) because of generally relatively low binding affinity (~mM) between noncognate glycans and glycan binding proteins (GBPs) (46). Nonetheless, these studies strongly suggested Y3 to be a GBP.

Figure 5E:
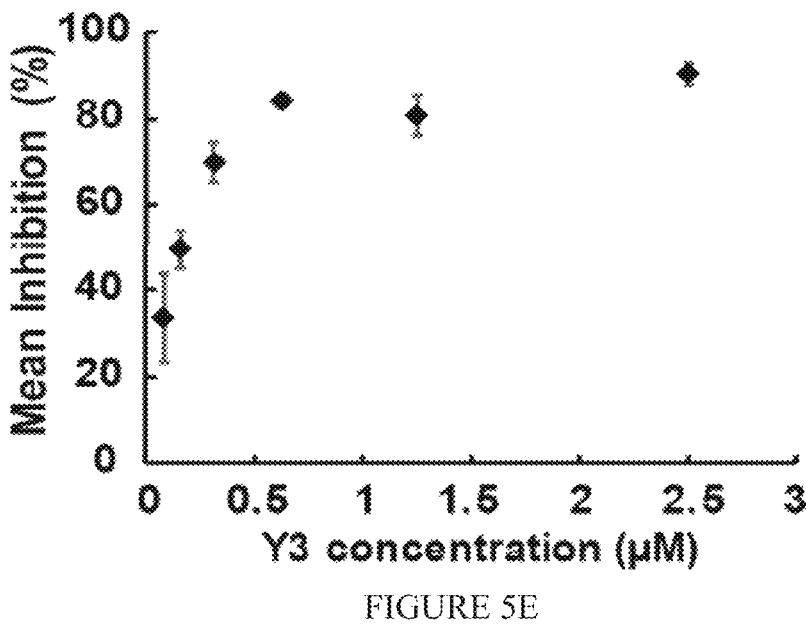
FIG. 5E shows inhibition of TMGMV infection by Y3.

The anti-TMV activity of recombinant Y3 was evaluates and showed that Y3 reduced the infectivity of purified Tobacco mild green mosaic virus (TMGMV) (26.5 µg/ml) by 50% at 0.12 µM (FIG. 5E), more effective than that reported for native Y3 and TMV (0.17 µM) (39). When mixed with TMGMV at room temperature and on ice, recombinant Y3 (0.078 µM) rapidly reduced the infectivity of TMGMV by 40% and 10.7%, respectively. A 20-min incubation period substantially increased the corresponding inhibition to 52.1% and 39.2%, suggesting the effects of both temperature and incubation time. Collectively, these data demonstrated that recombinant Y3 from the yeast system retained the proven anti-viral activity.

Example 2: Y3 Induced Caspase-Dependent Apoptosis of Human T-Cell Leukemia Jurkat Cells Given the diverse and important roles glycans play in cancer biology, potential cytotoxicity of Y3 against a panel of human cancer cell lines was assessed (Table 2).

TABLE 2

Selected cell lines in anticancer activity screening.

| Cell line | Types |
|---|---|
| Jurkat | T cell leukemia |
| DAN-G | pancreas carcinoma |
| MIA-PaCa-2 | pancreas carcinoma |
| DU145 | prostatic cancer |
| Hela | cervical cancer |
| HepG2 | liver carcinoma |
| UM-SCC-1 | head and neck squamous carcinoma |
| HEK 293 | non-malignant control |

Figures 7A, 7B:
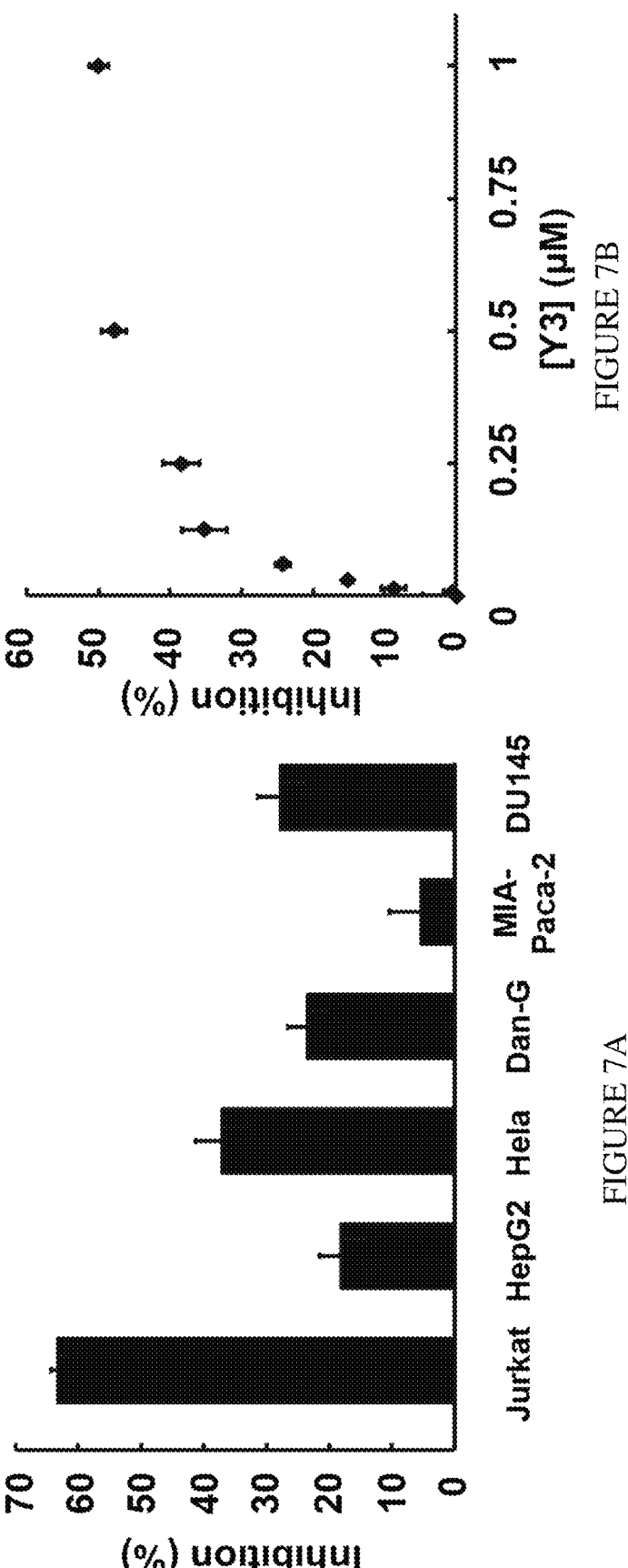
FIG. 7A shows an anticancer activity screening of Y3 by MTT assay.
FIG. 7B shows a dose-dependent inhibition of Jurkat cells by recombinant Y3.

At 10 µM concentration, Y3 showed only modest to weak growth inhibition of cervical cancer Hela cells, liver carcinoma HepG2 cells, pancreas carcinoma Dan-G cells, and prostatic cancer DU-145 cells (FIG. 7A). By contrast, however, Y3 exhibited potent activity toward human T-cell leukemia Jurkat cells at the nM level (FIG. 7B). The high selectivity was further indicated with no observed cytotoxic effect on pancreas carcinoma MIA-PaCa-2, kidney HEK293 and head and neck squamous carcinoma UM-SCC-1 cells.

Figure 6A:
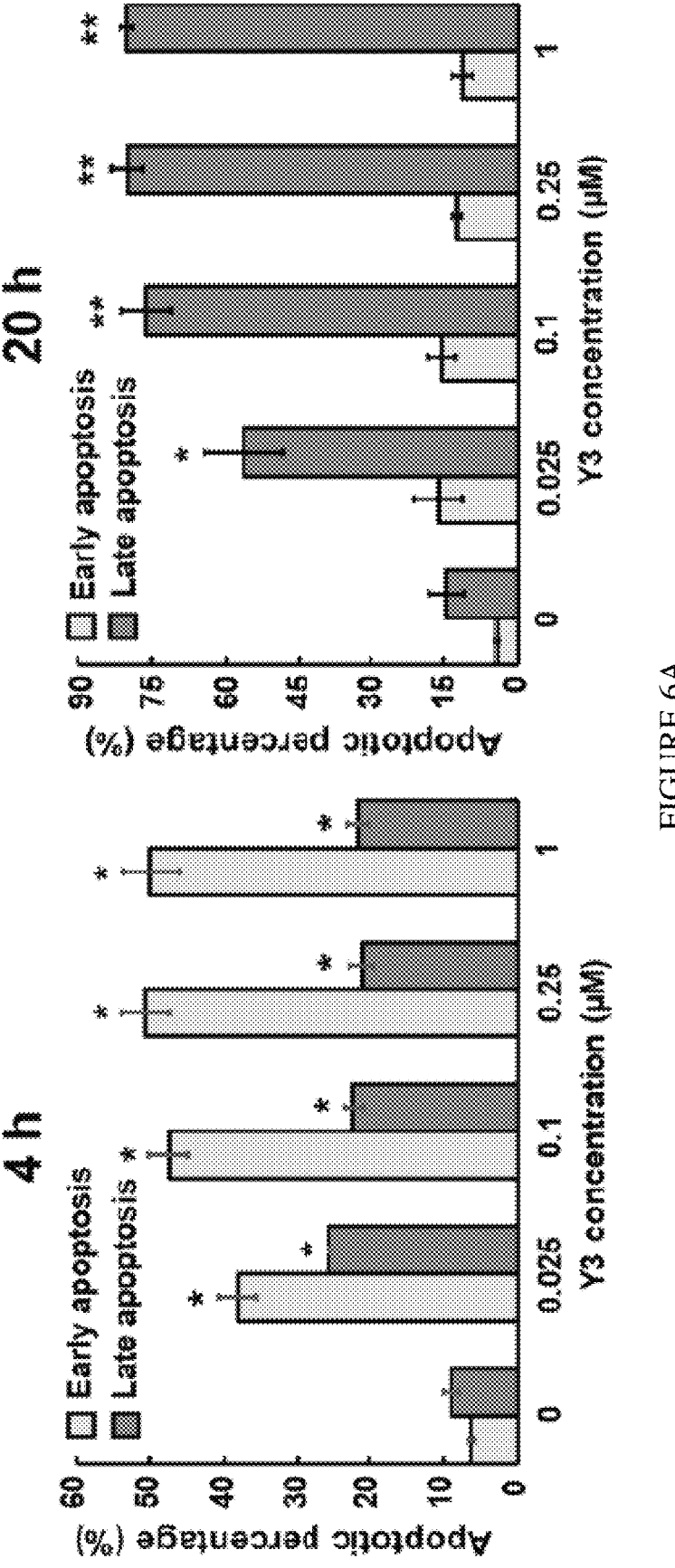
FIG. 6A shows Annexin V and 7-AAD staining of Jurkat cells after treatment with different concentrations of Y3.
Figure 8:
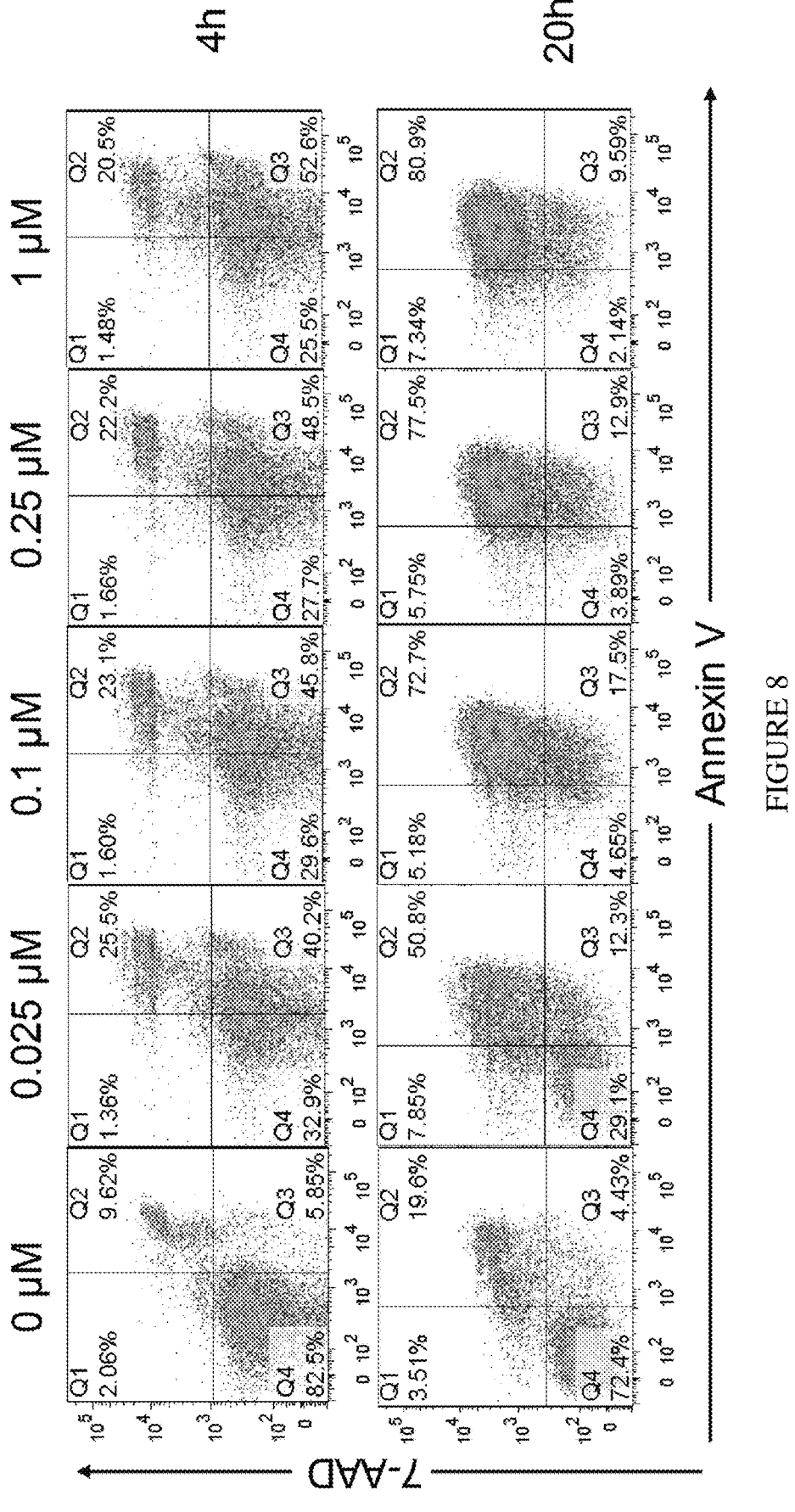
FIG. 8 shows the flow cytometry analysis of cell apoptosis by Y3 using Annexin V/7-AAD staining.

To further probe the effects of Y3 on Jurkat cells, the modes of cell death were examined using 7-aminoactinomycin D (7-AAD) and Annexin V double staining (47). This analysis revealed that Y3 induced both early and late apoptosis of Jurkat cells in a dose-dependent manner (FIG. 6A). Treatment at 0.1 µM for 4 h induced 45%±2.5% of Jurkat cells to enter early stage apoptosis as indicated by Annexin V staining, while 23%±1.3% were stained by both 7-AAD and Annexin V, suggesting late phase apoptosis (FIG. 6A and FIG. 8). These percentage values of early and late phase apoptosis were shifted to 17%±3.0% and 73%±4.8%, respectively, at 20 h, giving apoptotic cells as 90% of total cells. These findings indicate a potent and rapid cytotoxicity of Y3 against leukemia cells.

Figure 6B:
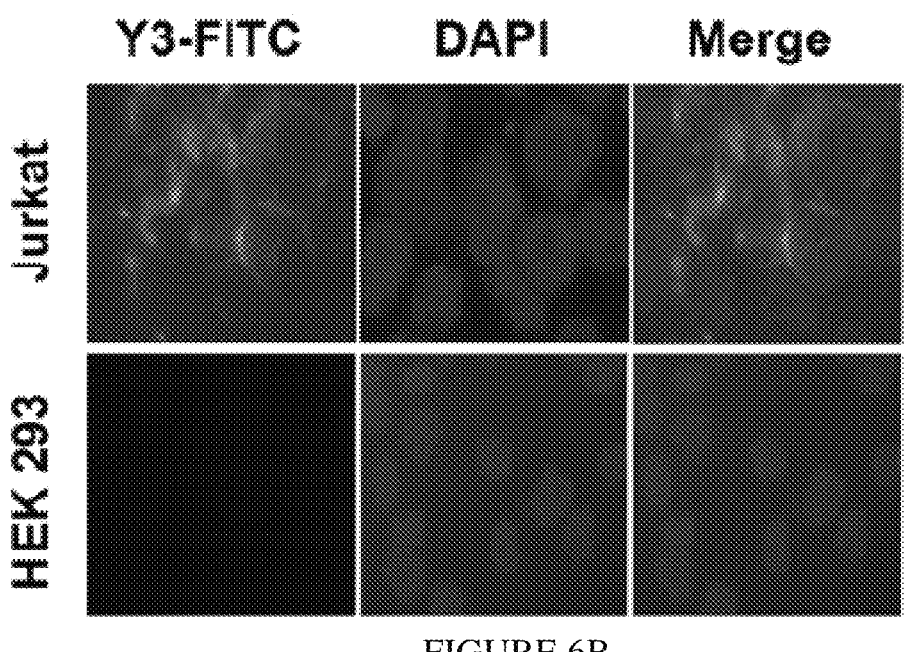
FIG. 6B shows fluorescence microscopy images of Jurkat cells and HEK 293 cells after treatment with Y3-FITC.

To further investigate this activity, recombinant Y3 was labeled with a fluorescein-5-isothiocyanate (FITC) fluorescent probe. FITC-Y3 retained a similar level of anti-Jurkat activity as observed with Y3 (FIG. 10A), and demonstrated to bind to the cell surface of Jurkat cells in a dose-dependent manner (FIG. 6 and FIG. 10B). No transport of FITC-Y3 into the cells was observed. By contrast, FITC-Y3 showed minimal binding to the control HEK293 cells (FIG. 6B). These results suggested that Y3 triggered the apoptosis pathways through the binding to the cell surface of Jurkat cells and highlighted potential applications in the management of acute T-cell leukemia.

Figure 6C:
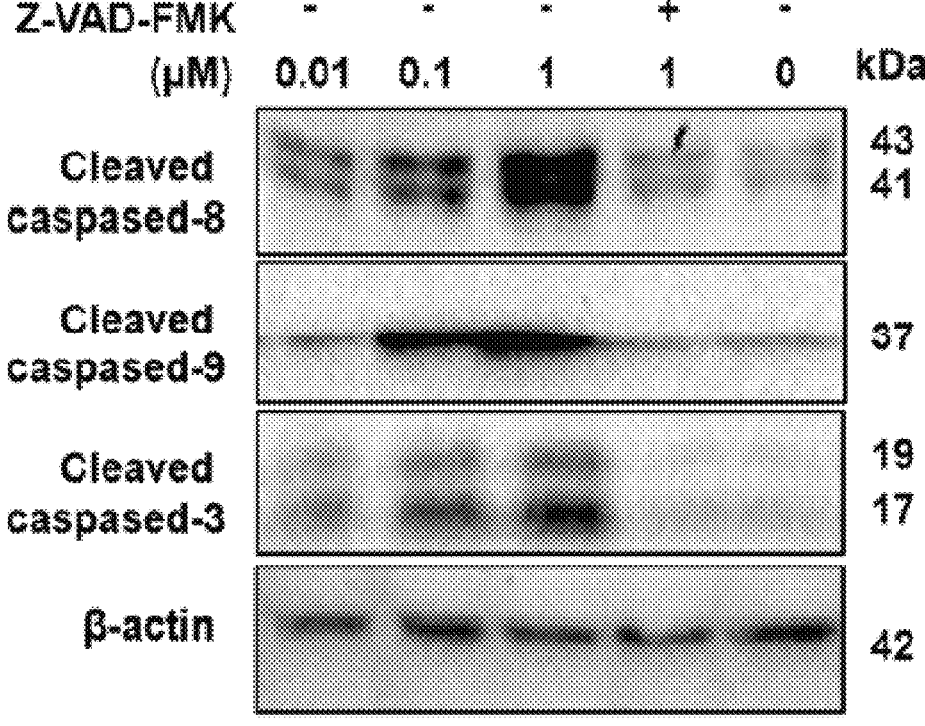
FIG. 6C shows western blot analysis of cleaved caspases in Jurkat cells treated with different concentrations of Y3 and Z-VAD-FMK.

The potential mechanism of the cytotoxicity of Y3 was examined. As the activation of caspases is essential in both intrinsic and extrinsic apoptotic pathways (48), the levels of cleaved caspases were measured in Jurkat cells after the treatment of Y3 at 0.01 to 1 µM for 20 h (FIG. 6C). Western blotting analysis clearly demonstrated that Y3 induced the activation of caspases 3, 8, and 9 in a dose-dependent manner, while co-treatment with the pan-caspase inhibitor z-VAD-FMK (20 μM) significantly blocked the activation of all three caspases, confirming a caspase-dependent mechanism of Y3's action (FIG. 6C).

Example 3: Glycan Binding Profile of Y3

Figure 9A:
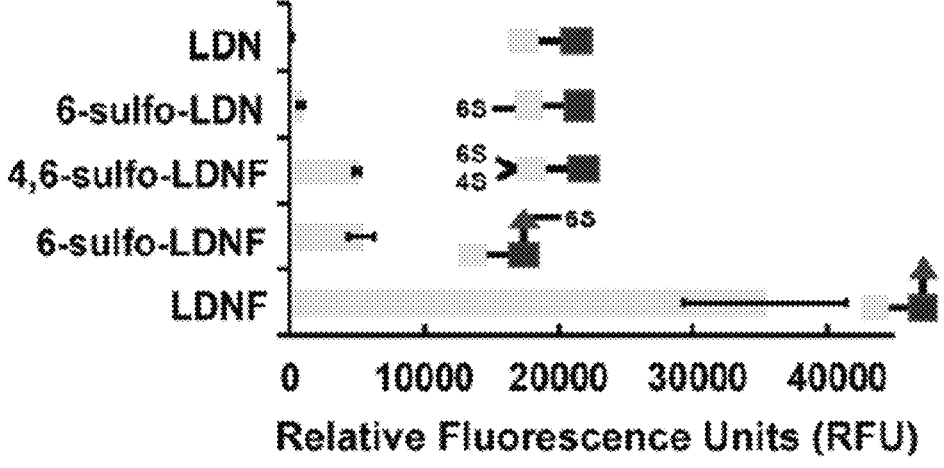
FIG. 9A shows the Y3-glycan binding profile of glycans of the LDN family.

Glycans are critical to various, essential molecular and cellular processes related to diseases and health, for example as important biomarkers and potential therapeutic and diagnostic targets of cancers (4-7). To assess the glycan binding profile of Y3, biotinylated Y3 was prepared to screen against a mammalian glycan array consisting of 600 glycans in replicates of six at the Consortium for Functional Glycomics. Detailed analysis of the concentration-dependent binding of Y3 showed the strongest binding affinity to GalNAcβ1-4(Fucα1-3)GlcNAc (LDNF) (FIG. 9A). LDNF is a member of the LacdiNAc (GalNAcβ1-4GlcNAc, LDN) family of glycans, which are abundant in invertebrates such as parasitic helminths and insects (49). In humans, the LDN-type glycans are less common and may be associated with the development of some cancers (50, 51). The binding affinity of the LDNF glycan epitope and Y3 was 10-100 times higher than closely related LDN or sulfated analogs that were included in the array (FIG. 9A). Additionally, 6'-sulfation of LDNF resulted in a weaker binding (~ eight times lower) while a 3-sulfation group completely blocked the glycan-Y3 interaction, illustrating a specific Y3-glycan interaction (FIG. 9A).

Figure 9B:
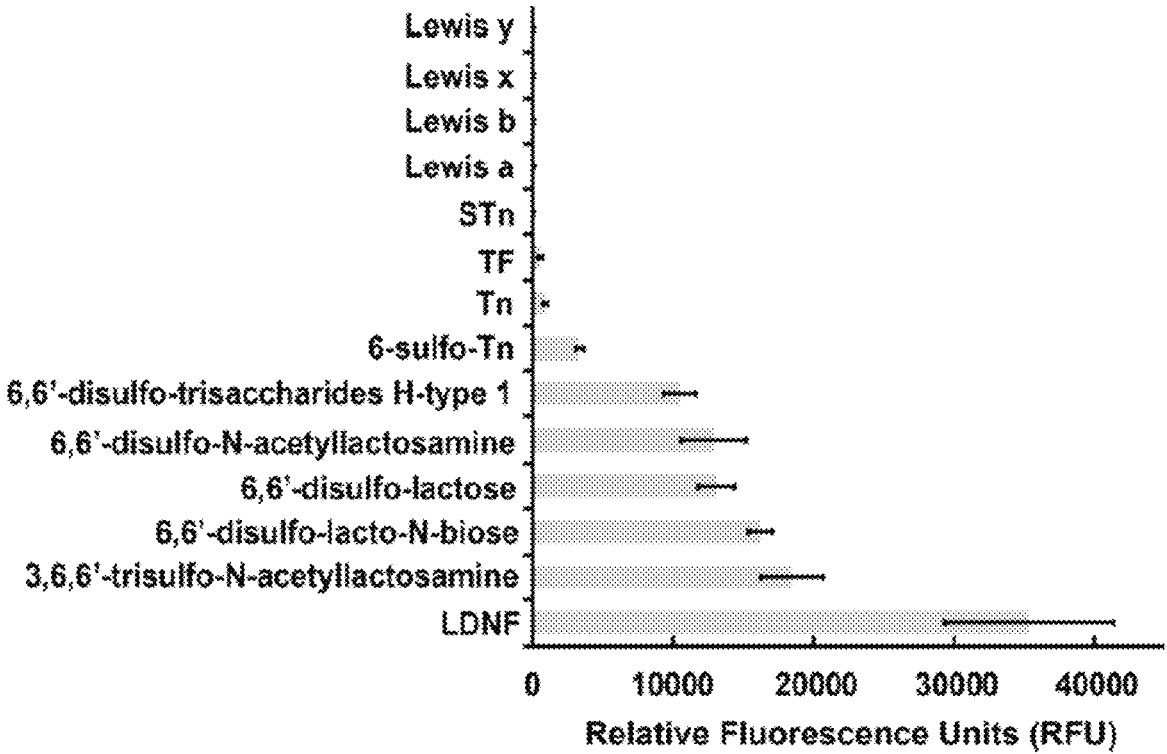
FIG. 9B shows the Y3-glycan binding profile of variety of glycans and common human antigens.

Furthermore, there was a distinct trend of sulfation in the top ligands of Y3, such as disaccharides 3,6,6'-trisulfo-N-acetyllactosamine, 6,6'-disulfo-lacto-N-biose, 6,6'-disulfo-lactose, 6,6'-disulfo-N-acetyllactosamine, and tri-saccharide Fucα1-2(6S)Galβ1-3(6S)GlcNAc (6',6''-disulfo-trisaccha-rides H-type 1) (FIG. 9B). In fact, sulfo modification occurred on the majority of top 20 glycans, suggesting that this group could mediate specific interactions with Y3 (Table 3).

TABLE 3

| Top 20 glycans from glycan microarray screening | | | | | | | |
|---|---|---|---|---|---|---|---|
| Y3 (5 μg/mL) | | | | Y3 (50 μg/mL) | | | |
| ID | Glycan | RFU | SD | ID | Glycan | RFU | SD |
| 97 | GalNAcb1-4(Fuca1-3)GlcNAcb-Sp0 | 16543 | 1302 | 97 | GalNAcb1-4(Fuca1-3)GlcNAcb-Sp0 | 35336 | 5997 |
| 45 | (6S)Galb1-4(6S)Glcb-Sp8 | 7075 | 845 | 22 | 6S(3S)Galb1-4(6S)GlcNAcb-Sp0 | 18424 | 2228 |
| 440 | (6S)Galb1-3(6S)GlcNAc-Sp0 | 6718 | 1217 | 440 | (6S)Galb1-3(6S)GlcNAc-Sp0 | 16181 | 864 |
| 22 | 6S(3S)Galb1-4(6S)GlcNAcb-Sp0 | 5634 | 774 | 45 | (6S)Galb1-4(6S)Glcb-Sp8 | 13063 | 1262 |
| 496 | Fuca1-2(6S)Galb1-3(6S)GlcNAcb-Sp0 | 4508 | 178 | 295 | (6S)Galb1-4(6S)GlcNAcb-Sp0 | 12862 | 2289 |
| 222 | Fuca1-2(6S)Galb1-4(6S)Glcb-Sp0 | 3871 | 136 | 496 | Fuca1-2(6S)Galb1-3(6S)GlcNAcb-Sp0 | 10464 | 1175 |
| 295 | (6S)Galb1-4(6S)GlcNAcb-Sp0 | 3820 | 628 | 222 | Fuca1-2(6S)Galb1-4(6S)Glcb-Sp0 | 9781 | 1200 |
| 39 | (6S)(4S)Galb1-4GlcNAcb-Sp0 | 2825 | 86 | 155 | Galb1-4(6S)Glcb-Sp0 | 8857 | 579 |
| 237 | Neu5Aca2-3Galb1-3(6S)GlcNAc-Sp8 | 2821 | 176 | 505 | Galb1-3(6S)GlcNAcb-Sp8 | 8805 | 1208 |
| 34 | (3S)Galb1-4(6S)GlcNAcb-Sp0 | 2801 | 205 | 495 | Fuca1-2Galb1-3(6S)GlcNAcb-Sp0 | 6445 | 580 |
| 35 | (3S)Galb1-4(6S)GlcNAcb-Sp8 | 2637 | 103 | 26 | (3S)Galb1-4(6S)Glcb-Sp0 | 6377 | 283 |
| 505 | Galb1-3(6S)GlcNAcb-Sp8 | 2471 | 613 | 237 | Neu5Aca2-3Galb1-3(6S)GlcNAc-Sp8 | 5929 | 532 |
| 495 | Fuca1-2Galb1-3(6S)GlcNAcb-Sp0 | 2450 | 579 | 39 | (6S)(4S)Galb1-4GlcNAcb-Sp0 | 5616 | 909 |
| 23 | 6S(3S)Galb1-4GlcNAcb-Sp0 | 2125 | 132 | 34 | (3S)Galb1-4(6S)GlcNAcb-Sp0 | 5538 | 877 |
| 498 | GalNAcb1-4(Fuca1-3)(6S)GlcNAcb-Sp8 | 2032 | 386 | 498 | GalNAcb1-4(Fuca1-3)(6S)GlcNAcb-Sp8 | 5351 | 940 |
| 27 | (3S)Galb1-4(6S)Glcb-Sp8 | 1792 | 431 | 23 | 6S(3S)Galb1-4GlcNAcb-Sp0 | 5251 | 1201 |
| 506 | (6S)(4S)GalNAcb1-4GlcNAc-Sp8 | 1679 | 95 | 506 | (6S)(4S)GalNAcb1-4GlcNAc-Sp8 | 4972 | 293 |
| 288 | Galb1-4(Fuca1-3)(6S)GlcNAcb-Sp0 | 1343 | 143 | 27 | (3S)Galb1-4(6S)Glcb-Sp8 | 4918 | 440 |
| 47 | (6S)GlcNAcb-Sp8 | 1325 | 169 | 375 | GalNAcb1-4GlcNAcb1-2Mana1-6(GalNAcb1-4GlcNAcb1-2Mana1-3)Manb1-4GlcNAcb1-4GlcNAc-Sp12 | 4180 | 285 |
| 42 | (6S)Galb1-4Glcb-Sp0 | 1302 | 452 | 40 | (4S)Galb1-4GlcNAcb-Sp8 | 3946 | 452 |

GlcNAc, Glc, or their 6-sulfated analogs appeared at the reducing end of all top 20 glycans of Y3. In fact, β-6-sulfo-GlcNAc was the best monosaccharide glycan in the Y3 glycan screening, whose signal was 11 times lower than LDNF (FIG. 9B). Also, Y3 strongly favored terminal, non-reducing GalNAc or Gal that are modified by mono- or di-sulfo groups at 6, 3 or 4 position (Table 2). However, Y3 showed only weak binding to GalNAc itself, also known as Tn antigen that is commonly found on cancer cells (52).

Other cancer-relevant Tn antigen derivatives including the Thomsen-Friedenreich antigen (TF antigen, Galβ1-3Gal-NAc) and sialyl Tn antigen (STn antigen, Neu5Acα2-6GalNAc) also showed minimal binding to Y3 (FIG. 9B). Glycan profiling of Y3 further suggested that a β1,3-glycosidic bond was favored slightly over a β1,4-linkage (e.g., 6,6'-disulfo-N-acetyllactosamine vs. 6,6'-disulfo-lacto-N-biose, FIG. 9B). However, Y3 demonstrated minimal binding to either β1-3 bond-containing histo-blood group antigens Lewis a [Galβ1-3(Fucα1-4)GlcNAc] and Lewis b [Fucα1-2Galβ1-3(Fucα1-4)GlcNAc] or β1-4 bond-related cancer antigens Lewis x [Galβ1-4(Fucα1-3)GlcNAc] and Lewis y [Fucα1-2Galβ1-4(Fucα1-3)GlcNAc] (FIG. 9B). Strikingly, the only structural difference between LDNF and Lewis x is the terminal GalNAc and Gal, which varies their binding affinities toward Y3 at 50 µg/mL by over 17,000 times (FIG. 9B). Overall, the glycan screening suggested that Y3 exclusively recognized the LDNF moiety and modestly interacted with sulfated di- or tri-saccharides primarily consisting of GalNAc, Gal, GlcNAc, Glc, Fuc, and their sulfated analogs. According to current knowledge, two Ca2+-dependent lectins macrophage galactose-type lectin (MGL) and dendritic cell-specific C-type lectin DC-SIGN are the only other characterized GBPs that show a relatively tight interaction with LDNF (53, 54). However, MGL binds to the LDN antigen 1.3 times more tightly than LDNF, while DC-SIGN shows significantly stronger interaction with Lewis x (55), marking Y3 as the only known LDNF-specific GBP.

Example 4: High Resolution Crystal Structure of Y3

To gain structural insights into Y3 as a specific LDNF-binding GBP, its crystal structure was determined by single-wavelength anomalous diffraction analysis (SAD) (Table 4).

TABLE 4

X-ray data collection, processing and structure refinement.

| Data Collection | Y3-Native | Y3-Derivative |
|---|---|---|
| Resolution range (Å) | 41.8-1.18 | 41.3-1.70 |
| | (1.22-1.18)* | (1.76-1.70)* |
| Space group | P2₁ | P2₁ |
| a b c (Å), β (°) | 53.3 56.1 62.7, 92.7 | 41.1 55.2 41.0, 99.5 |
| Total No. of reflections | 567305 (38773) | 148850 (11787) |
| Unique reflections | 113409 (9627) | 20217 (1790) |
| Multiplicity | 5.0 (4.0) | 7.4 (6.6) |
| Completeness | 93% (80%) | 99% (87%) |
| $<I/\sigma(I)>$ | 22.98 (4.44) | 14.57 (3.70) |
| Wilson B factor (Å²) | 8.1 | 14.0 |
| $R_{merge}^{\dagger}$ | 0.041 (0.29) | 0.093 (0.44) |
| $R_{meas}^{\dagger}$ | 0.046 (0.34) | 0.099 (0.48) |
| $CC_{1/2}^{\dagger}$ | 1 (0.91) | 1 (0.93) |

| Refinement | Y3-Native | Y3-Derivative |
|---|---|---|
| $R_{work}^{\dagger}$ | 0.172 (0.205) | 0.159 (0.187) |
| $R_{free}^{\dagger}$ | 0.189 (0.240) | 0.194 (0.248) |
| No. of non-H atoms | 4189 | 1950 |
| Protein | 3420 | 1751 |
| Ligand | 52 | 34 |
| Protein residues | 448 | 224 |
| RMS Bonds (Å) | 0.006 | 0.019 |
| RMS Angles (°) | 1.05 | 1.54 |
| Ramachandran | | |
| Favored (%) | 97 | 95 |
| Outliers (%) | 0 | 0 |
| Clashscore | 1.3 | 2.9 |
| Average B factors (Å²) | 11.9 | 18.0 |
| Protein | 10.0 | 16.9 |

TABLE 4-continued

X-ray data collection, processing and structure refinement.

| | | |
|---|---|---|
| Ligand | 14.9 | 30.5 |
| Water | 20.7 | 27.2 |

*Values for the outer shell are given in parentheses $\dagger R_{merge} = E_{hkl}\Sigma_i I_i(hkl) - \langle\langle I(hkl)\rangle/\Sigma_{hkl} \quad \Sigma_i I_i(hkl); \quad R_{meas} = \left(\sum_{hkl}\sqrt{n/(n-1)}\sum_{i=1}^{n}|I_i(hkl) - \langle I(hkl)\rangle|\right)/\sum_{hkl}\sum_i I_i(hkl),$ where $I_i(hkl)$ is the ith intensity measurement of a reflection, $\langle I(hkl)\rangle$ is the average intensity value of that reflection and the summation is over all measurements. $CC_{1/2} = \Sigma(x - \langle x\rangle)(y - \langle y\rangle)/\sqrt{\Sigma(x - \langle x\rangle)^2 \Sigma(y - \langle y\rangle)^2}$. R-factor $= E_{hkl}|F_{obs}| - |F_{calc}|/E_{hkl}|F_{obs}|$, where $F_{obs}$ and $F_{calc}$ are measured and calculated structure factors, respectively. $R_{free}$ calculated from 5% of the reflections that were selected randomly and omitted during refinement.

Figure 13:
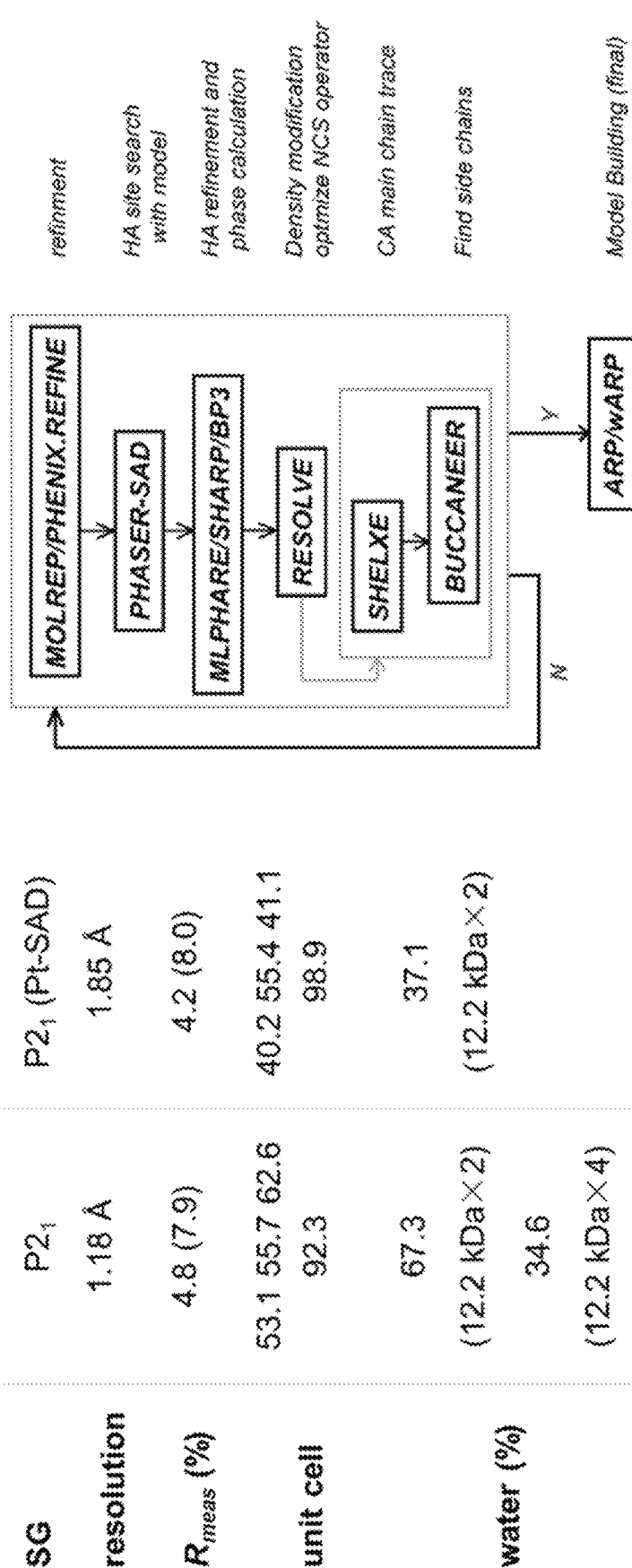
FIG. 13 shows the structural determination via Pt-SAD.

Native Y3 crystal diffracted to 1.2 Å resolution (P21, a=53.3 Å, b=56.1 Å, c=62.7 Å, β=92.7°) bearing translational noncrystallographic symmetry. Heavy atom soaking of crystals resulted in an orphan dataset (Y3-Pt) in an alternative lattice (P21, a=41.1 Å, b=55.2 Å, c=41.0 Å, β=99.5°) and for experimental phasing in the absence of any reference structure suitable for molecular replacement (FIG. 13). Depending on the lattices, Y3 consisted of one or two dimers per asymmetric unit.

Figure 14A:
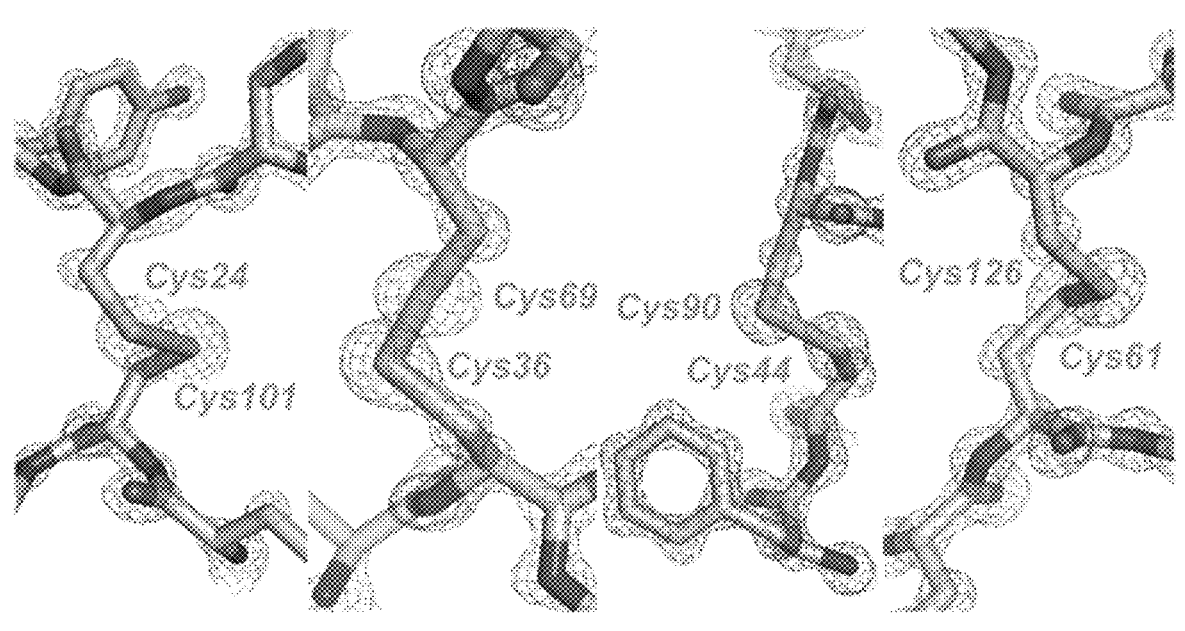
FIG. 14A shows the high-resolution crystal structure of Y3 including four intramolecular disulfide bridges that stabilize Y3 monomers.
Figure 14B:
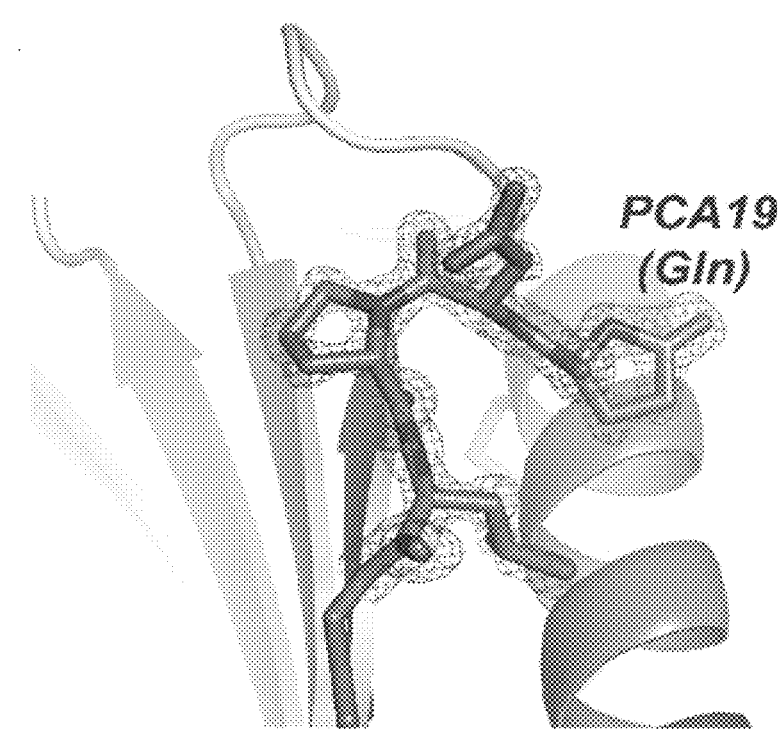
FIG. 14B shows PCA19 formation through Gln19 cyclization after the N-terminal Met was cleaved during Y3 expression.
Figure 14C:
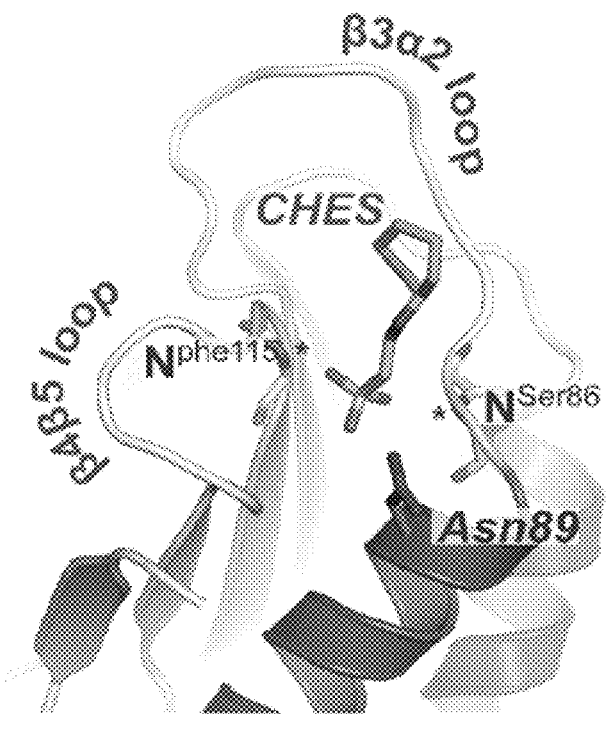
FIG. 14C shows the resolution of a bound CHES molecule near β4β5 and β3α2 loops.
Figure 14D:
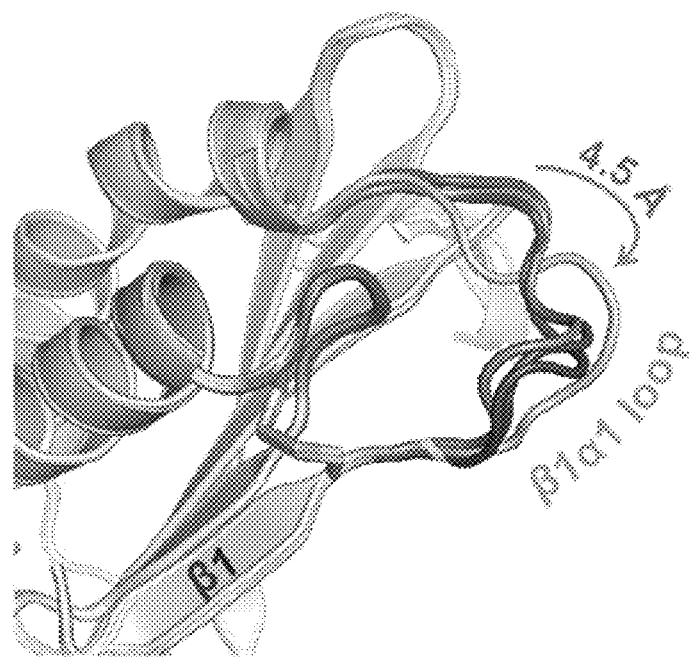
FIG. 14D shows Y3 monomers with the loops of other monomers.
Figure 14E:
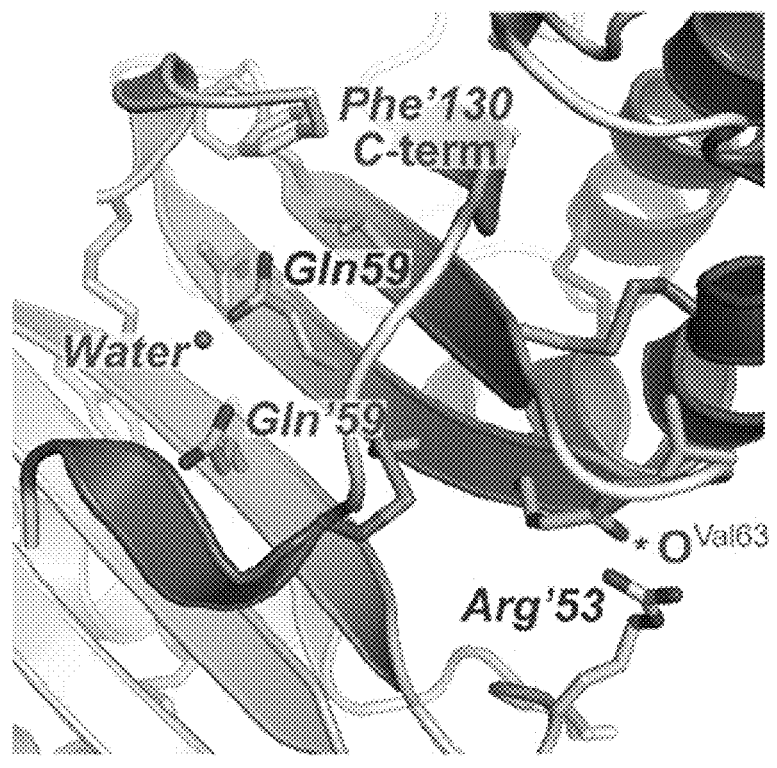
FIG. 14E shows Y3 dimer formation through a β-β interaction.
Figures 16A, 16B:
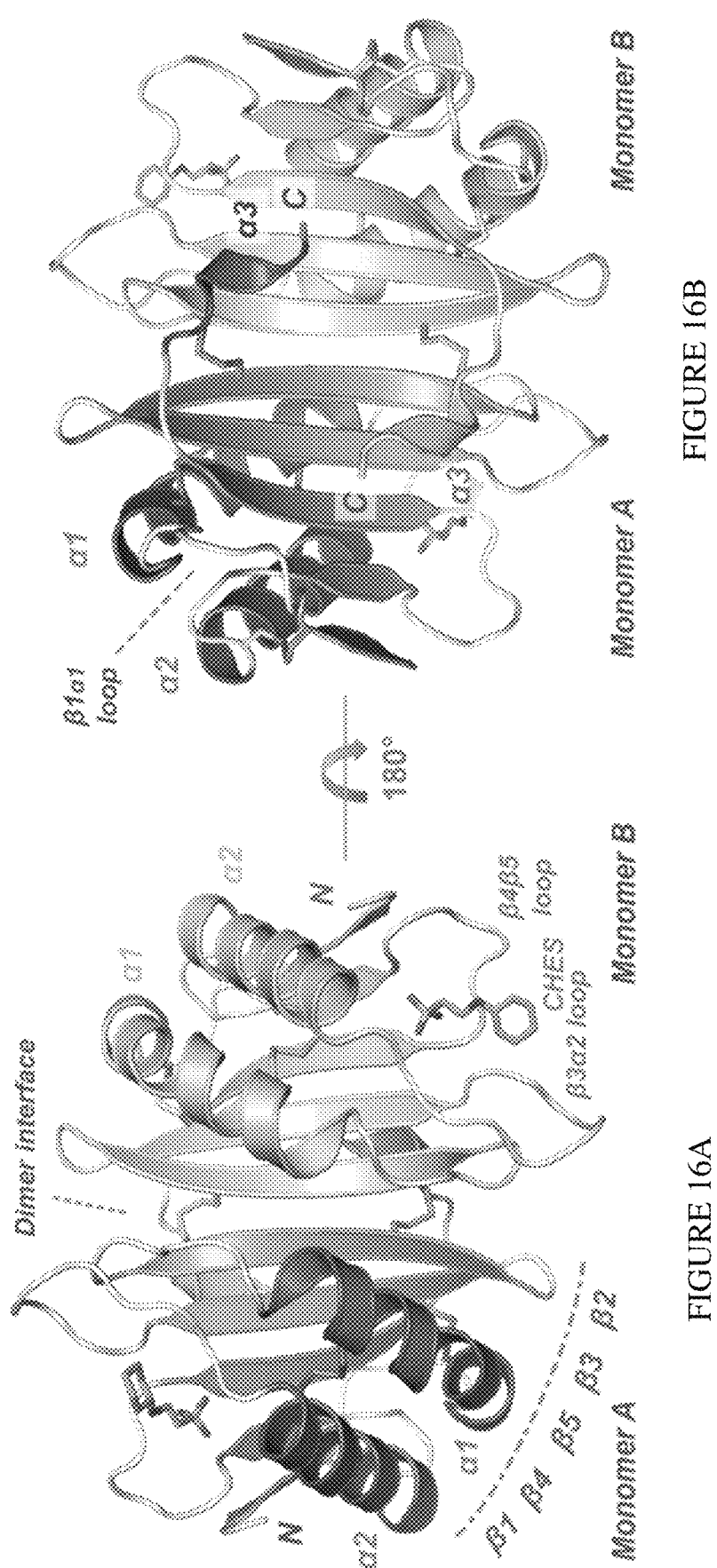
FIG. 16A shows the crystal structure of a Y3 dimer.
FIG. 16B shows the crystal structure of the Y3 dimer rotated by 180°.
Figure 16C:
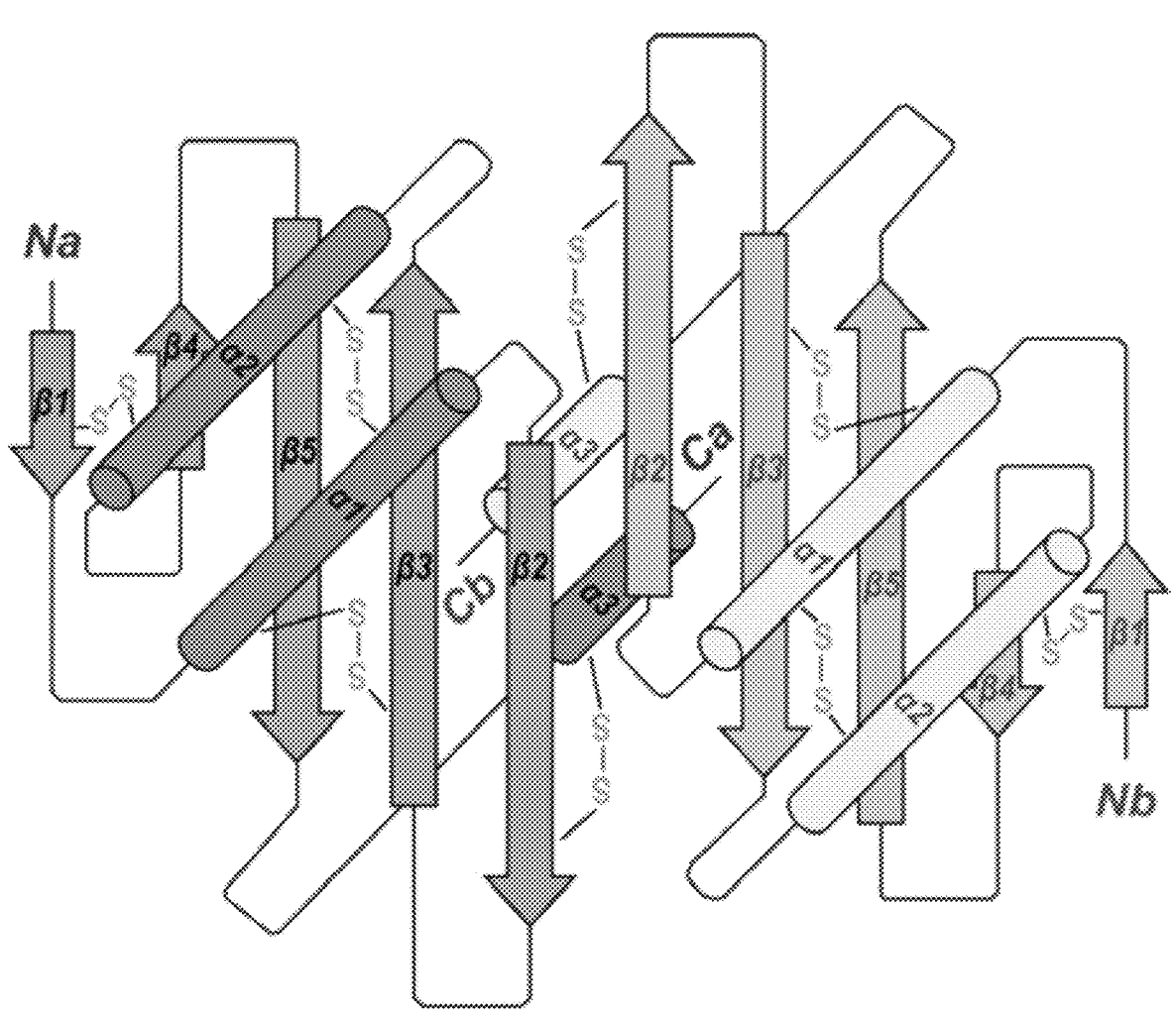
FIG. 16C shows a structure topology illustration of a Y3 dimer with the indication of disulfide bridges.

Y3 monomer forms a compact single-domain αβα-sandwich consisting of three α-helices and a five-stranded β-sheet (FIG. 16A). The β-sheet was linked as β1-β4-β5-β3-β2 from edge to center in an antiparallel orientation. Two long α-helices (α1 and α2) pack against one side of the β-sheet, while the C-terminal α3 is located on the opposite side. The monomer contains four-intramolecular disulfide bridges, Cys24-Cys101, Cys36-Cys69, Cys61-Cys126, and Cys44-Cys90 (FIG. 14A and FIG. 16B), agreeing with the results of Ellman's (FIG. 2) and MS analysis (FIG. 5D). The majority of these disulfide bridges are amongst conserved cysteines through Y3 homologs from other fungal species (FIG. 5A). Another modification on Y3 was the formation of pyroglutamic acid (PCA) from Gln19 presumably by a glutamine cyclase after translation (56) (FIG. 14B), as not uncommonly observed on +1 residue following the signal peptide. Also, one molecule of N-cyclohexyl-2-aminoethanesulfonic acid (CHES) from the crystallization buffer was clearly resolved between the β3α2 and β4β5 loops (FIG. 14C). Its anionic sulfate group interacted with NPhe115, NSer86 and the Asn89 sidechain while the hydrophobic cyclohexane extended into the bulk solvent. In the crystallographic asymmetric unit, the four Y3 monomers had an RMSD range of 0.14-0.36 Å (among monomers) and differed primarily in the β1α1 loop regions (residues 26-31), with a Cα (backbone carbon) movement of up to 4.5 Å in this region (FIG. 14D). The five-stranded, anti-parallel β-sheets from two Y3 monomers assembled to a large, intermolecular ten-stranded, antiparallel β-sheet with all α1 and α2 helices on one side and α3 on the opposite side (FIG. 16A). Additional dimeric interactions included intermolecular hydrogen bonds between Arg'53 of the α1β2 loop and the neighboring Val63, and water-mediated H-bonds between Gln59/Gln'59 (FIG. 14E).

Figure 15A:
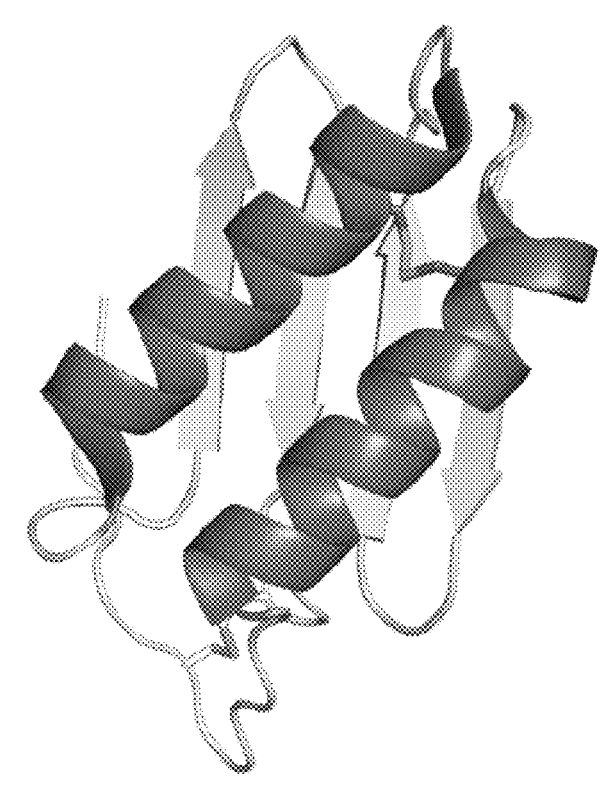
FIG. 15A shows LDL (pdb entry 4NDV) monomer that shares a similar structure with Y3.
Figure 15B:
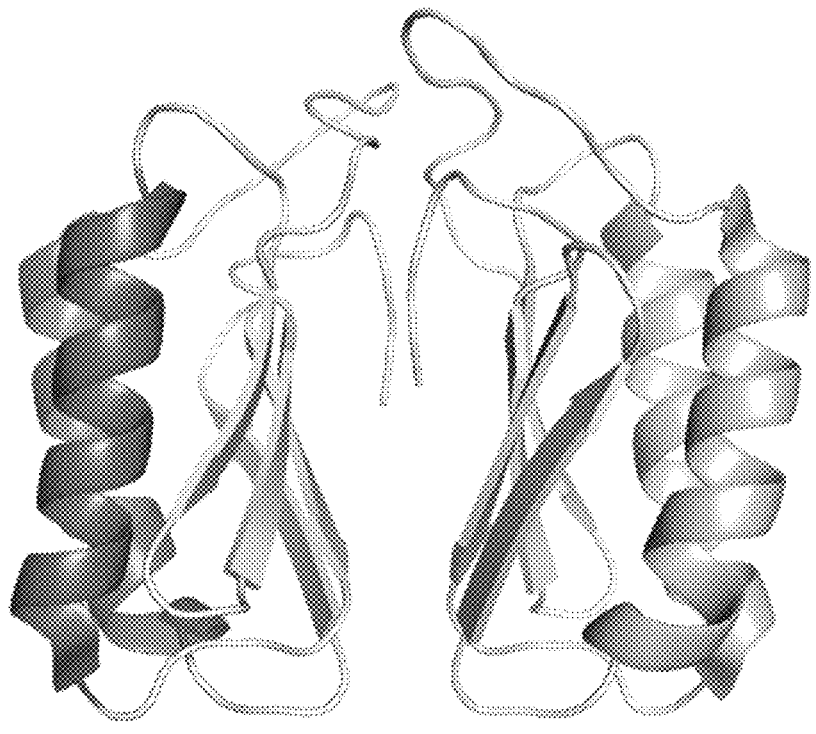
FIG. 15B shows LDL dimerized in a different fashion with Y3.

Structural homology searches (DALI server) (57) revealed that Y3 shares limited structural similarity with known structures. The most relevant in overall structural homology is an α-Gal binding lectin LDL from mushroom *Lyophyllum decastes* (PDB ID: 4NDV, Z-score 8.7, RMSD 2.2 Å) (58), which shares 12% sequence identity with Y3 (FIG. 15A). The LDL structure contains a four-stranded, antiparallel β-sheet and two α-helices being packed against one side of the β-sheet. However, the structure of Y3 shows significant differences with LDL, including the number and locations of disulfide bridges, the number of β-sheets and the α3 helix present in Y3. Importantly, LDL forms an alternate dimer by the stacking of the exposed sides of the β-strands of the two subunits as an αβ$_2$α sandwich (59) (FIG. 15B). By contrast, the Y3 monomer is featured with the presence of α3 and is incompatible of forming such β-stack-β conformation. Finally, even 1 mM of Y3 did not agglutinate human and rabbit erythrocytes (FIG. 11), strikingly different with the characteristic feature of other reported lectins. All of these structural and functional findings indicated that Y3 adopts a novel glycan-binding mode.

Example 5: Glycan Binding Site of Y3

Figure 17A:
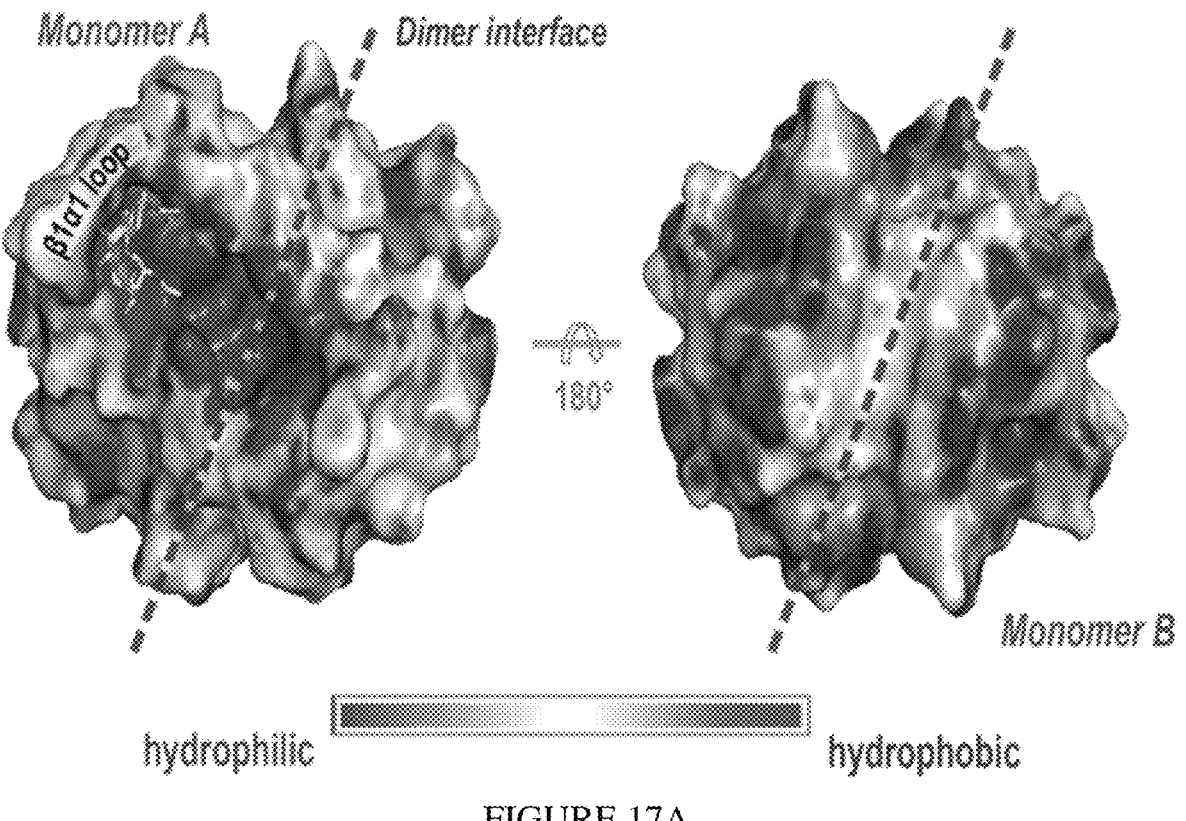
FIG. 17A shows the putative glycan binding pocket of Y3. Left: electrostatic surface representation of the Y3 dimer; right: the Y3 dimer rotated by 180°.

The Y3 dimer forms a Janus conformation with the majority of hydrophilic residues assembled on one side. The other surface forms a hydrophilic pocket that sits on the ten-stranded, antiparallel β-sheet and is surrounded by the two α3 helices, one from each monomer (FIG. 17A). The large pocket is a unique feature comparing with other reported GBPs and suggests that Y3 most likely interacts with complex glycan chains rather than mono- or di-saccharides. Indeed, GalNAc, 6-sulfo-GlcNAc, D-Man, D-Glu, D-Gal, D-Fuc or D-Lac did not show an interaction with Y3 using isothermal titration calorimetry or bio-layer interferometry analysis. Additionally, soaking of Y3 crystals with any of these sugars did not allow clear interpretable ligand electron difference maps. These results are consistent with the glycan binding array data suggesting LDNF as a favored ligand.

Figure 17B:
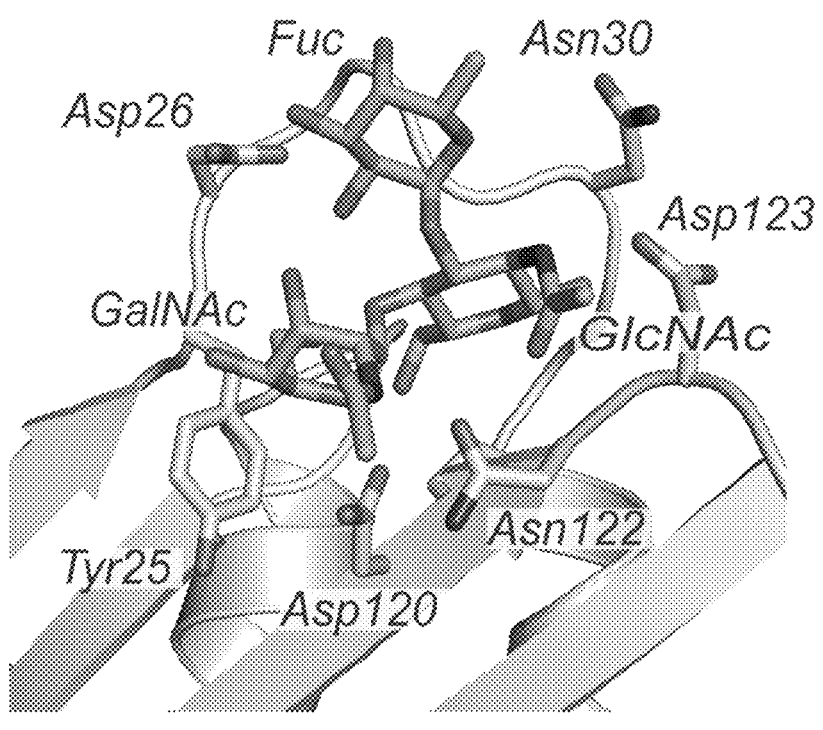
FIG. 17B shows a close-up view of the binding site with docked LDNF.
Figure 17C:
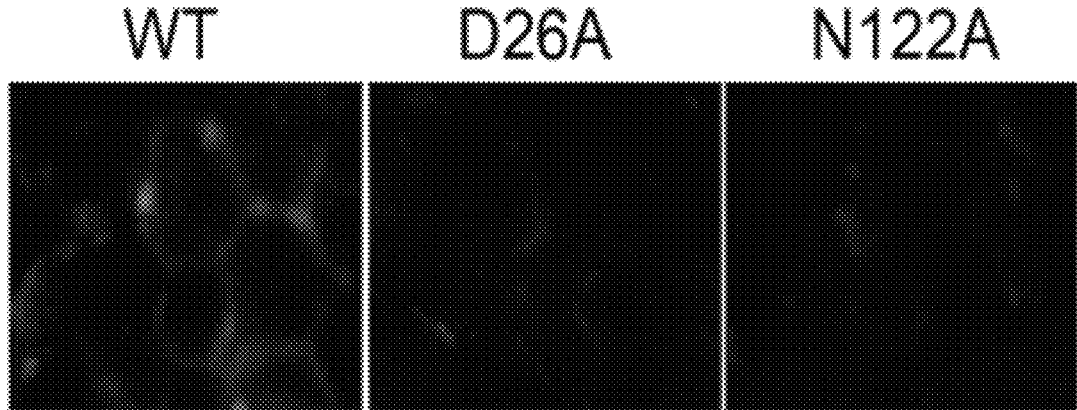
FIG. 17C shows fluorescence microscopy images of Jurkat cells after treatment with FITC-labeled Y3, Y3D26A, and Y3N122A.
Figures 17D, 18:
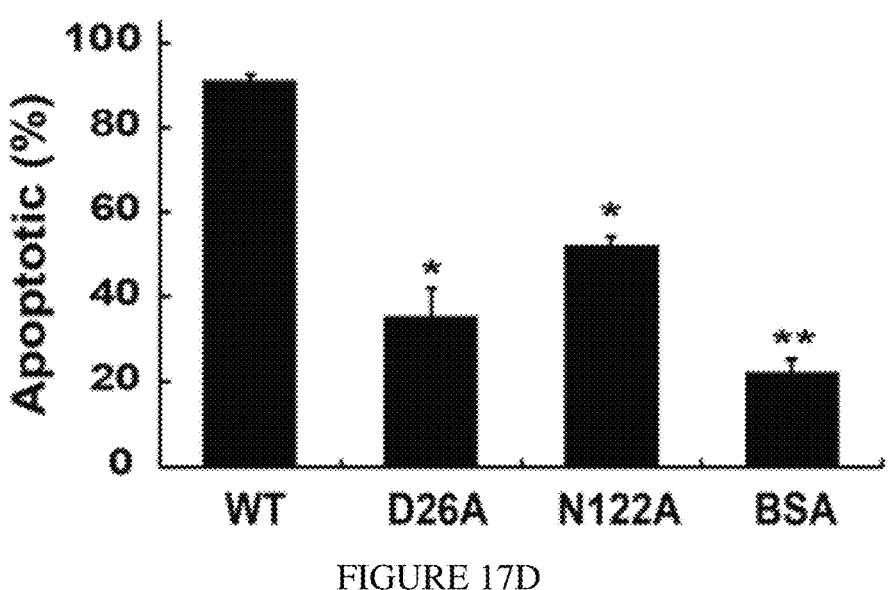
FIG. 17D shows an Annexin V/7-AAD apoptosis assay.
FIG. 18 shows GlcNAc binding in the structure of *Wisteria floribunda* lectin (PDB 5KXC) and *Clitocybe nebularis* ricin B-like lectin (PDB 3NBE).
Figure 19:
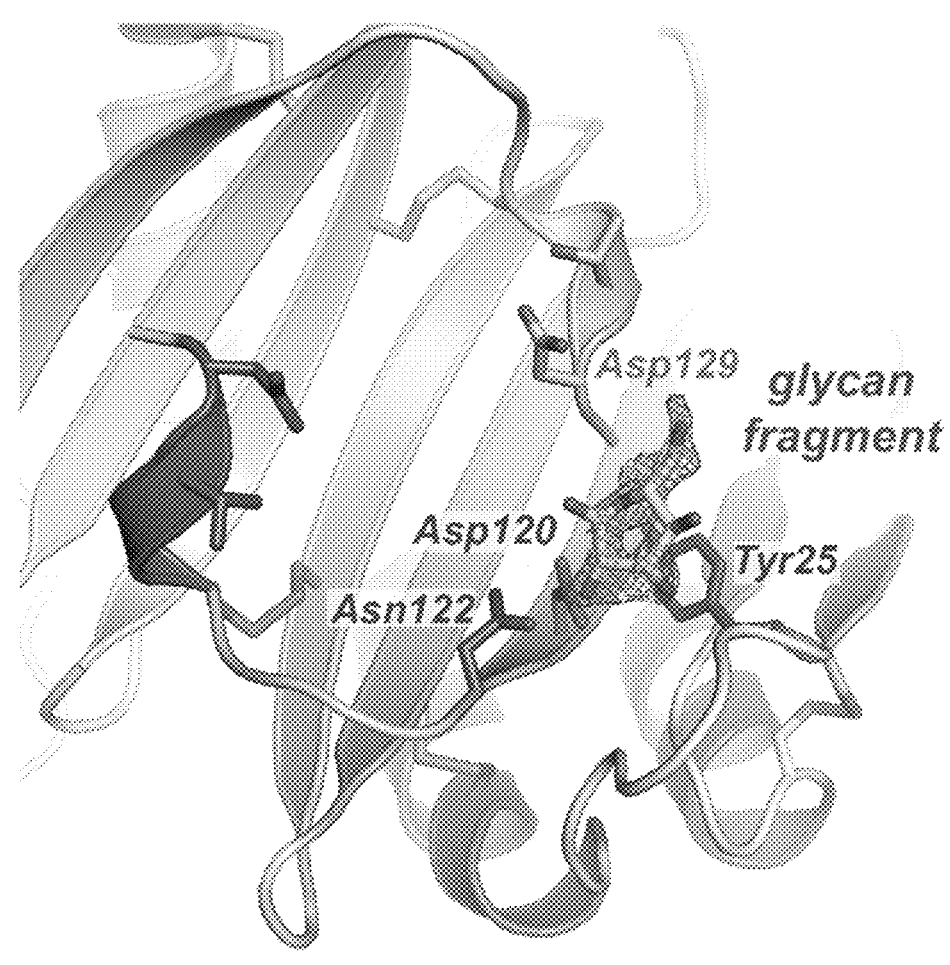
FIG. 19 shows an unassigned electron density near the GlcNAc interacting region in Y3 high-resolution structure.

To provide additional insights into the Y3/glycan recognition, the LDNF structure was modeled into the Y3 dimer (FIG. 17B). LDNF was aligned along the β1α1 loop in the top docking result. Key hydrogen bond interactions between the protein and sugar include Asp26, Asn30, Asp120, Asn122, and Asp123. The GlcNAc moiety sits in the cavity between the β3 and the β1α1 loop, and the terminal GalNAc is near Asp120/Asn122 forming an interaction with Tyr25 (FIG. 17B). The similar interaction mode with GlcNAc is present in the structures of *Wisteria floribunda* lectin (PDB 5KXC) and *Clitocybe nebularis* ricin B-like lectin (PDB 3NBE) (60) (FIG. 18). In addition, the LDNF motif could further extend to the dimeric interface of Y3 leading to improved glycan binding affinity. Of note, an unassigned electron density near the GlcNAc interacting region was observed in the high-resolution structure (FIG. 17A and FIG. 19). The density most likely corresponds to a polysaccharide fragment of bound endogenous glycan (likely mannose), indirectly supporting the instant docking model and agreeing with the results of phenol sulfuric acid and ESI-MS analysis (FIG. 3 and FIG. 4). To provide a structure/function relationship of key residues in ligand binding, Y3 D26A and N122A mutants were created (FIG. 19). Both mutants nearly lost their ability to bind Jurkat cells (FIG. 17C). Furthermore, the cytotoxicity of both mutants was significantly decreased as compared to the level of a negative control BSA (FIG. 17D). These results provided strong supportive evidence to the instant docking model, and offered new insights into the specific interactions of Y3-LDNF. After binding to the glycan, Y3 can initiate apoptosis pathways in Jurkat cells.

In conclusion, these studies characterized Y3 from the edible mushroom *C. comatus* as a novel GBP with a unique topology and tertiary structure. Its cytotoxicity toward Jurkat cells was mediated by the activation of caspase cascade that was induced by specific LDNF/Y3 interactions. The critical need of an improved treatment regimen of aggressive acute T-cell leukemia lends obvious significance to Y3 for developing potential novel treatment and diagnosis options.

Example 6: Mechanism of Y3 Mediated Activation-Induced Cell Death (AICD) of T-Cells As mentioned throughout this disclosure, Y3 is a small protein isolated from the edible mushroom *C. comatus*. Y3 is a founding member of a new family of glycan binding proteins and Y3 possesses potent cytotoxicity towards human T-cell leukemia Jurkat cells likely through caspase-dependent apoptosis. To further elucidate the cellular mechanisms of Y3's actions on Jurkat cells, whole-cell transcriptomic studies were performed to examine the changes of gene expression profiling of Jurkat cells upon Y3 stimulation. Y3 may effectively induce T-cell activation processes in Jurkat cells, which might lead to activation-induced cell death (AICD). In this regard, Y3 can serve as a useful tool to probe the mechanism of T-cell activation and constitutes a novel therapeutic agent for T-cell related cancers.

Y3 May Initiate T Cell Activation

Figure 20A:
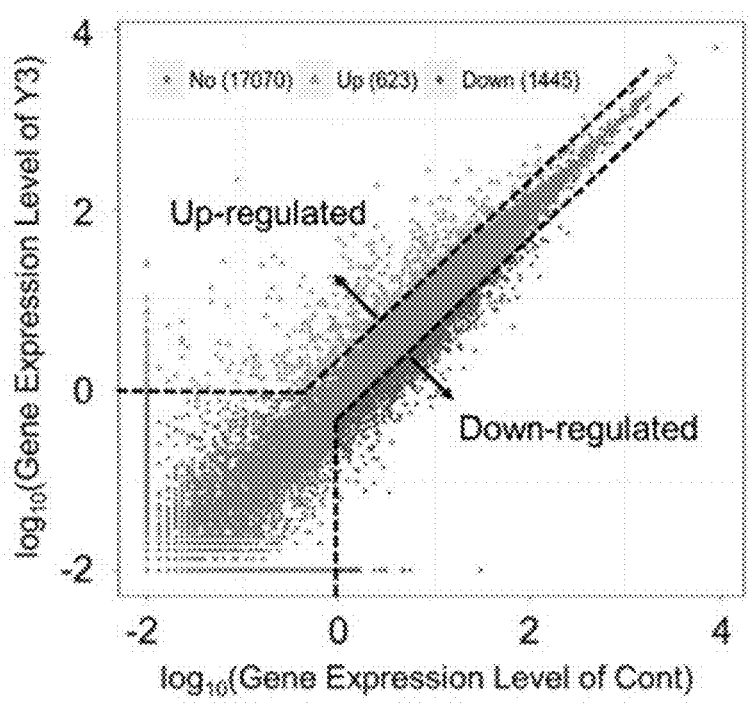
Figure 20B:
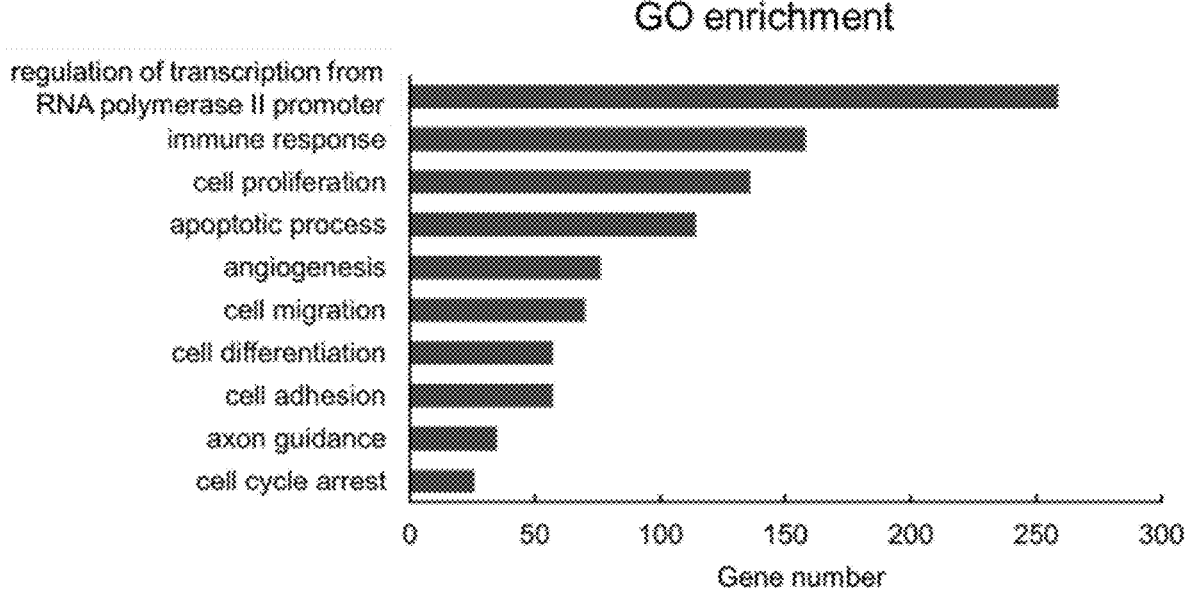

RNA sequencing (RNA-Seq) has emerged as a powerful technology enabling the systemic evaluation of gene expression profiles. This approach was employed to gain a comprehensive picture of gene expression changes in Jurkat cells affected by Y3. Comparison of the gene expression profiles between Y3 treated and control (PBS) treated groups revealed 2068 differentially expressed genes (DEGs), with 623 up-regulated and 1445 down-regulated (FIG. 20A). These DEGs were then clustered and evaluated by Gene ontology (GO) enrichment analysis. The top 10 terms in this analysis were highly related to T-cell activation, including regulation of transcription from RNA polymerase II promoter, immune response, cell proliferation, apoptotic process, angiogenesis, cell migration, cell differentiation, cell adhesion, axon guidance, and cell cycle arrest (FIG. 20B). In line with these results, a large panel of top regulated genes encodes cytokines, including various interleukins, tumor necrosis factors and chemokines (FIG. 20C). The released cytokines are centrally important to T-cell activation as they promote proliferation, differentiation or apoptosis of activated T cells. Therefore, the whole-cell transcriptomic studies indicate that Y3 likely initiates the activation of Jurkat cells.

Figure 21:
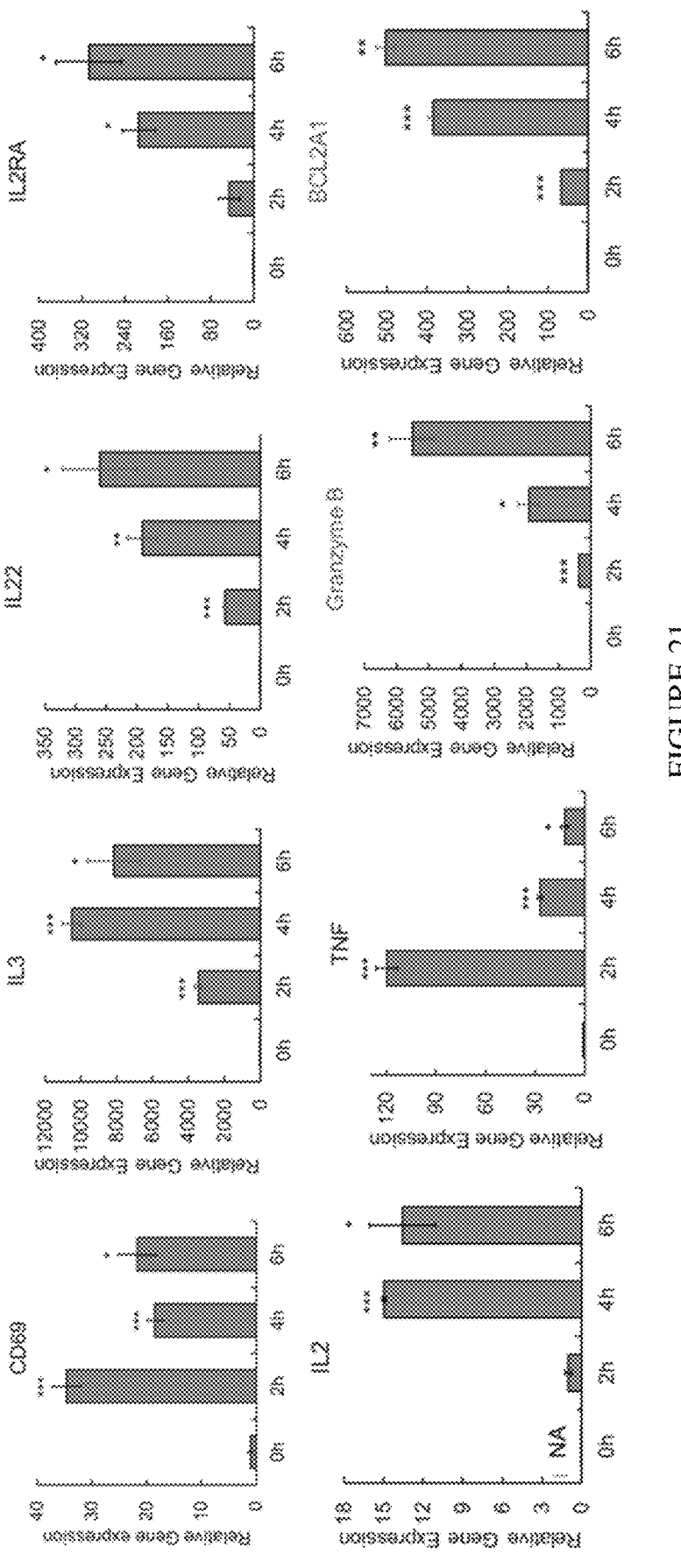
FIG. 21 shows that RT-qPCR analysis validated the upregulated expression of select T-cell activation biomarker genes in Jurkart cells upon Y3 treatment. Data are shown as the means±SD (n=6). Significant differences between 0 h and other time points are shown (*P<0.05; P<0.01; *P<0.001).

To validate the results of RNA-seq analysis, RT-qPCR was performed to quantitate the expression of several T-cell activation biomarker genes. CD69 is an early activation marker expressed in T cells. Upon Y3 treatment, the expression level of CD69 gene peaked at 2 h with a 34-fold increase (FIG. 21). Also, Y3 treatment significantly increased the expression levels of interleukins IL2, IL3, IL2RA and IL22 (15 to 11,000 times, FIG. 21), which is featured in T-cell activation as they promote cell growth and differentiation. In addition, tumor necrosis factor (TNF), Bcl-2 family member BCL2A1 and Granzyme B were significantly upregulated by Y3 (tens to thousands of times, FIG. 21). These biomarkers can mediate apoptosis of highly activated Jurkat cells. Collectively, these RT-qPCR results indicated that Y3 may stimulate the activation of Jurkat cells and cause activation-induced cell death.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

1. Varki A (2017) Biological roles of glycans. *Glycobiology* 27:3-49.

2. Moremen K W, Tiemeyer M, Nairn A V (2012) Vertebrate protein glycosylation: diversity, synthesis and function. *Nat Rev Mol Cell Bio* 13:448-462.

3. Hart G W (2013) Thematic minireview series on glycobiology and extracellular matrices: glycan functions pervade biology at all levels. *J Biol Chem* 288:6903-6903.

4. Pinho S, SReis C A (2015) Glycosylation in cancer: mechanisms and clinical implications. *Nat Rev Cancer* 15:540-555.

5. Stowell S R, Ju T, Cummings R D (2015) Protein glycosylation in cancer. *Annu Rev Pathol* 10:473-510.

6. Dube D H, Bertozzi C R (2005) Glycans in cancer and inflammation—potential for therapeutics and diagnostics. *Nat Rev Drug Discov* 4:477-488.

7. Hung T C, Lin C W, Hsu T L, Wu C Y, Wong C H (2013) Investigation of SSEA-4 binding protein in breast cancer cells. *J Am Chem Soc* 135:5934-5937.

8. Potapenko I O, et al. (2010) Glycan gene expression signatures in normal and malignant breast tissue; possible role in diagnosis and progression. *Mol Oncol* 4:98-118.

9. Sharon N (2007) Lectins: carbohydrate-specific reagents and biological recognition molecules. *J Biol Chem* 282: 2753-2764.

10. Sharon N, Lis H (2004) History of lectins: from hemagglutinins to biological recognition molecules. *Glycobiology* 14:53R-62R.

11. Gabius H J, Andre S, Jimenez-Barbero J, Romero A, Solis D (2011) From lectin structure to functional glycomics: principles of the sugar code. *Trends Biochem Sci* 36:298-313.

12. Hassan M A, Rouf R, Tiralongo E, May T W, Tiralongo J (2015) Mushroom lectins: specificity, structure and bioactivity relevant to human disease. *Int J Mol Sci* 16:7802-7838.

13. Le Coq J, Ghosh P (2011) Conservation of the C-type lectin fold for massive sequence variation in a *Treponema* diversity-generating retroelement. *Proc Natl Acad Sci USA* 108:14649-14653.

14. Grant O C, Woods R J (2014) Recent advances in employing molecular modelling to determine the specificity of glycan-binding proteins. *Curr Opin Struct Biol* 28:47-55.

15. Taylor M E, Drickamer K (2014) Convergent and divergent mechanisms of sugar recognition across kingdoms. *Curr Opin Struct Biol* 28:14-22.

16. Saghatelian A, Couso J P (2015) Discovery and characterization of smORF-encoded bioactive polypeptides. *Nat Chem Biol* 11:909-916.

17. Camby I, Le Mercier M, Lefranc F, Kiss R (2006) Galectin-1: a small protein with major functions. *Glycobiology* 16:137R-157R.

18. Barondes S H, et al. (1994) Galectins: a family of animal beta-galactoside-binding lectins. *Cell* 76:597-598.

19. Wadler C S, Vanderpool C K (2007) A dual function for a bacterial small RNA: SgrS performs base pairing-dependent regulation and encodes a functional polypeptide. *Proc Natl Acad Sci USA* 104:20454-20459.

20. Kastenmayer J P, et al. (2006) Functional genomics of genes with small open reading frames (sORFs) in *S. cerevisiae*. *Genome Res* 16:365-373.

21. Ramamurthi K S, Storz G (2014) The small protein floodgates are opening; now the functional analysis begins. *BMC Biol* 12:96.

22. Ruiz-Orera J, Messeguer X, Subirana J A, Alba M M (2014) Long non-coding RNAs as a source of new peptides. *Elife* 3:e03523.

23. Ma J, et al. (2016) Improved identification and analysis of small open reading frame encoded polypeptides. *Anal Chem* 88:3967-3975.

24. Huang H, et al. (2015) A general strategy for the discovery of metabolic pathways: D-threitol, L-threitol, and erythritol utilization in *Mycobacterium smegmatis*. *J Am Chem Soc* 137:14570-14573.

25. Siegel R L, Miller K D, Jemal A (2016) Cancer statistics, 2016. *CA Cancer J Clin* 66:7-30.

26. Belver L, Ferrando A (2016) The genetics and mechanisms of T cell acute lymphoblastic leukaemia. *Nat Rev Cancer* 16:494-507.

27. Chiaretti S, Foa R (2009) T-cell acute lymphoblastic leukemia. *Haematologica* 94:160-162.

28. Maude S L, Teachey D T, Porter D L, Grupp S A (2015) CD19-targeted chimeric antigen receptor T-cell therapy for acute lymphoblastic leukemia. *Blood* 125:4017-4023.

29. Greaves M (2016) Leukaemia 'firsts' in cancer research and treatment. *Nat Rev Cancer* 16:163-172.

30. Charlier E, et al. (2010) SHIP-1 inhibits CD95/APO-1/Fas-induced apoptosis in primary T lymphocytes and T leukemic cells by promoting CD95 glycosylation independently of its phosphatase activity. *Leukemia* 24:821-832.

31. Erjavec J, Kos J, Ravnikar M, Dreo T, Sabotic J (2012) Proteins of higher fungi—from forest to application. *Trends in Biotechnology* 30:259-273.

32. Hibbett D S, et al. (2007) A higher-level phylogenetic classification of the fungi. *Mycol Res* 111:509-547.

33. Lindequist U, Niedermeyer T H, Julich W D (2005) The pharmacological potential of mushrooms. *Evid Based Complement Alternat Med* 2:285-299.

34. Kirst H A (2013) Developing new antibacterials through natural product research. *Expert Opin Drug Dis* 8:479-493.

35. Tanasova M, Sturla S J (2012) Chemistry and biology of acylfulvenes: sesquiterpene-derived antitumor agents. *Chem Rev* 112:3578-3610.

36. Buchel E, Mayer A, Martini U, Anke H, Sterner 0 (1998) Structure elucidation of omphalotin, a cyclic dodecapeptide with potent nematicidal activity isolated from *Omphalotus olearius*. *Pestic Sci* 54:309-311.

37. Xu X, Yan H, Chen J, Zhang X (2011) Bioactive proteins from mushrooms. *Biotechnol Adv* 29:667-674.

38. Kumar A, et al. (2002) An integrated approach for finding overlooked genes in yeast. *Nat Biotechnol* 20:58-63.

39. Wu L, Wu Z, Lin Q, Xie L (2003) Purification and activities of an alkaline protein from mushroom *Coprinus comatus*. *Wei Sheng Wu Xue Bao* 43:793-798.

40. Li B, Lu F, Suo X, Nan H (2010) Antioxidant properties of cap and stipe from *Coprinus comatus*. *Molecules* 15:1473-1486.

41. Fan J, et al. (2006) Structural elucidation of a neutral fucogalactan from the mycelium of *Coprinus comatus*. *Carbohydr Res* 341:1130-1134.

42. Ellman G L (1959) Tissue sulfhydryl groups. *Arch Biochem Biophys* 82:70-77.

43. Masuko T, et al. (2005) Carbohydrate analysis by a phenol-sulfuric acid method in microplate format. *Anal Biochem* 339:69-72.

44. Dubois M, Gilles K A, Hamilton J K, Rebers P A, Smith F (1956) Colorimetric method for determination of sugars and related substances. *Anal Chem* 28:350-356.

45. Tateno H, Winter H C, Petryniak J, Goldstein I J (2003) Purification, characterization, molecular cloning, and expression of novel members of jacalin-related lectins from rhizomes of the true fern *Phlebodium aureum* (L) J. Smith (Polypodiaceae). *J Biol Chem* 278:10891-10899.

46. Liao J H, et al. (2016) A multivalent marine lectin from *Crenomytilus grayanus* possesses anti-cancer activity through recognizing globotriose Gb3. *J Am Chem Soc* 138:4787-4795.

47. George T C, et al. (2004) Distinguishing modes of cell death using the ImageStream®) multispectral imaging flow cytometer. *Cytom Part A* 59a:237-245.

48. Elmore S (2007) Apoptosis: a review of programmed cell death. *Toxicol Pathol* 35:495-516.

49. Nyame A K, Leppanen A M, Bogitsh B J, Cummings R D (2000) Antibody responses to the fucosylated Lacdi-NAc glycan antigen in *Schistosoma mansoni*-infected mice and expression of the glycan among schistosomes. *Exp Parasitol* 96:202-212.

50. Machado E, et al. (2011) N-Glycosylation of total cellular glycoproteins from the human ovarian carcinoma SKOV3 cell line and of recombinantly expressed human erythropoietin. *Glycobiology* 21:376-386.

51. Hirano K, Matsuda A, Shirai T, Furukawa K (2014) Expression of LacdiNAc groups on N-glycans among human tumors is complex. *Biomed Res Int* 2014:981627

52. Ju T Z, Aryal R P, Kudelka M R, Wang Y C, Cummings R D (2014) The Cosmc connection to the Tn antigen in cancer. *Cancer Biomark* 14:63-81.

53. van Vliet S J, et al. (2005) Carbohydrate profiling reveals a distinctive role for the C-type lectin MGL in the recognition of helminth parasites and tumor antigens by dendritic cells. *Int Immunol* 17:661-669.

54. van Die I, et al. (2003) The dendritic cell-specific C-type lectin DC-SIGN is a receptor for *Schistosoma mansoni* egg antigens and recognizes the glycan antigen Lewis x. *Glycobiology* 13:471-478.

55. van Liempt E, et al. (2006) Specificity of DC-SIGN for mannose- and fucose-containing glycans. *FEBS Lett* 580: 6123-6131.

56. Huang K F, Liu Y L, Cheng W J, Ko T P, Wang A H (2005) Crystal structures of human glutaminyl cyclase, an enzyme responsible for protein N-terminal pyroglutamate formation. *Proc Natl Acad Sci USA* 102:13117-13122.

57. Holm L, Rosenstrom P (2010) DALI server: conservation mapping in 3D. *Nucleic Acids Res* 38:W545-549.

58. van Eerde A, Grahn E M, Winter H C, Goldstein I J, Krengel U (2015) Atomic-resolution structure of the alpha-galactosyl binding *Lyophyllum decastes* lectin reveals a new protein family found in both fungi and plants. *Glycobiology* 25:492-501.

59. Goldstein I J, et al. (2007) A new alpha-galactosyl-binding protein from the mushroom *Lyophyllum decastes*. *Arch Biochem Biophys* 467:268-274.

60. Pohleven J, et al. (2012) Bivalent carbohydrate binding is required for biological activity of *Clitocybe nebularis* Lectin (CNL), the N, N'-diacetyllactosediamine (GalNAc beta1-4GlcNAc, LacdiNAc)-specific lectin from basidiomycete *C. nebularis*. *J Biol Chem* 287:10602-10612.

61. Smith D F, Song X Z, Cummings R D (2010) Use of glycan microarrays to explore specificity of glycan-binding proteins. *Method Enzymol* 480:417-444.

62. Anonymous (2006) The condensed protocols: from molecular cloning: a laboratory manual (Cold Spring Harbor Laboratory Press, Cold Spring Harbor, N.Y.) pp V, 800 p.

63. Xie C, et al. (2015) Irisin Controls Growth, Intracellular Ca2+Signals, and Mitochondrial Thermogenesis in Cardiomyoblasts. PLoS One 10:e0136816.

64. Ferrell J, Charudattan R, Elliott M, Hiebert E (2008) Effects of selected herbicides on the efficacy of tobacco mild green mosaic virus to control tropical soda apple (*Solanum* warm). Weed Sci 56:128-132.

65. Yang L, Connaris H, Potter J A, Taylor G L (2015) Structural characterization of the carbohydrate-binding module of NanA sialidase, a pneumococcal virulence factor. Bmc Struct Biol 15:15.

66. Kabsch W (2010) Integration, scaling, space-group assignment and post-refinement. Acta Crystallogr D 66:133-144.

67. Winn M D, et al. (2011) Overview of the CCP4 suite and current developments. Acta Crystallogr D 67:235-242.

68. Sheldrick G M (2010) Experimental phasing with SHELXC/D/E: combining chain tracing with density modification. Acta Crystallogr D Biol Crystallogr 66:479-485.

69. Cowtan K (2010) Recent developments in classical density modification. Acta Crystallogr D Biol Crystallogr 66:470-478.

70. McCoy A J, et al. (2007) Phaser crystallographic software. J Appl Crystallogr 40:658-674.

71. Abrahams J P Leslie A G W (1996) Methods used in the structure determination of bovine mitochondrial F-1 ATPase. Acta Crystallogr D 52:30-42.

72. Cowtan K (2006) The Buccaneer software for automated model building. 1. Tracing protein chains. Acta Crystallogr D 62:1002-1011.

73. Langer G, Cohen S X, Lamzin V S, Perrakis A (2008) Automated macromolecular model building for X-ray crystallography using ARP/wARP version 7. *Nat Protoc* 3:1171-1179.

74. Emsley P Cowtan K (2004) Coot: model-building tools for molecular graphics. Acta Crystallogr D 60:2126-2132.

75. Murshudov G N, et al. (2011) REFMAC5 for the refinement of macromolecular crystal structures. Acta Crystallogr D 67:355-367.

76. Afonine P V, et al. (2012) Towards automated crystallographic structure refinement with phenix.refine. Acta Crystallogr D 68:352-367.

77. Morris G M, et al. (2009) AutoDock4 and AutoDockTools4: Automated Docking with Selective Receptor Flexibility. J Comput Chem 30:2785-2791.

78. Shao Y, et al. (2006) Advances in methods and algorithms in a modern quantum chemistry program package. Phys Chem Chem Phys 8:3172-3191.

We claim:

1. A method of killing leukemia cells in a subject, the method comprising: administering to a subject having leukemia a composition comprising a recombinant Y3 protein, wherein the recombinant Y3 protein comprises the sequence set forth in SEQ ID NO: 3 and lacks amino acid residues 1-18 of SEQ ID NO: 1.

2. The method of claim 1, wherein the subject is a human.

3. The method of claim 1, wherein the recombinant Y3 protein is conjugated to one or more marker molecules.

4. The method of claim 1, wherein the recombinant Y3 protein is conjugated to one or more therapeutic molecules.

5. The method of claim 3, wherein the marker molecule is a molecule that emits a radioactive or a fluorescent signal.

6. The method of claim 4, wherein the therapeutic molecule is a radioactive molecule, a cytotoxic molecule, an apoptosis-inducing molecule, an antisense oligonucleotide, doxorubicin, 5-fluorouracil, methotrexate, pyrrolobenzodiazepine, calicheamicin, maytanisinoid, ausristatin, pyrrolobenzodiazepine, mertansine/emtansine, ravtansine/soravtansine, vincristine, vinblastine, etoposide, melphalan, mitomycin C, chlorambucil, daunorubicin, ricin, a thalidomide or a thalidomide analog, dolastatin, trichothecene, enediyne, taxane, anthracycline, adriamycin, vindesine, vinca alkaloid, teniposide, carminomycin, aminopterin, dactinomycin, bleomycin, esperamicin, tubulysin, cryptophycin, erlotinib, bortezomib, fulvestrant, sunitinib, letrozole, imatinib mesylate, oxaliplatin, leucovorin, rapamycin, lapatinib, lonafarnib, sorafenib, gefitinib, capecitabine, duocarmycin, lexitropsin, nitrosourea, platinol, purine antimetabolite, puromycin, steroid, purine antagonist, androgen, 5-azacytidine, azathioprine, busulfan, buthionine sulfoximine, camptothecin, carboplatin, carmustine, estrogen, 5-fluordeoxyuridine, gramicidin D, hydroxyurea, idarubicin, ifosfamide, irinotecan, lomustine, mechlorethamine, mithramycin, mitoxantrone, nitroimidazole, plicamycin, procarbizine, streptozotocin, tenoposide, 6-thioguanine, topotecan, vinorelbine, acyclovir, gangcyclovir, zidovudine, vidarabine, ribavarin, azidothymidine, cytidine arabinoside, amantadine, dideoxyuridine, iododeoxyuridine, poscarnet, or trifluridine.

7. A method of killing leukemia cells in a subject, the method comprising: administering to a subject having leukemia a composition comprising a recombinant *Coprinus comatus* Y3 protein consisting of amino acid residues 24 to 126 of SEQ ID NO: 1.

8. The method of claim 7, wherein the subject is a human.

9. The method of claim 7, wherein the recombinant *Coprinus comatus* Y3 protein is conjugated to one or more marker molecules.

10. The method of claim 7, wherein the recombinant *Coprinus comatus* Y3 protein is conjugated to one or more therapeutic molecules.

11. The method of claim 9, wherein the marker molecule is a molecule that emits a radioactive or a fluorescent signal.

12. The method of claim 10, wherein the therapeutic molecule is a radioactive molecule, a cytotoxic molecule, an apoptosis-inducing molecule, an antisense oligonucleotide, doxorubicin, 5-fluorouracil, methotrexate, pyrrolobenzodiazepine, calicheamicin, maytanisinoid, ausristatin, pyrrolobenzodiazepine, mertansine/emtansine, ravtansine/soravtansine, vincristine, vinblastine, etoposide, melphalan, mitomycin C, chlorambucil, daunorubicin, ricin, a thalidomide or a thalidomide analog, dolastatin, trichothecene, enediyne, taxane, anthracycline, adriamycin, vindesine, vinca alkaloid, teniposide, carminomycin, aminopterin, dactinomycin, bleomycin, esperamicin, tubulysin, cryptophycin, erlotinib, bortezomib, fulvestrant, sunitinib, letrozole, imatinib mesylate, oxaliplatin, leucovorin, rapamycin, lapatinib, lonafarnib, sorafenib, gefitinib, capecitabine, duocarmycin, lexitropsin, nitrosourea, platinol, purine antimetabolite, puromycin, steroid, purine antagonist, androgen, 5-azacytidine, azathioprine, busulfan, buthionine sulfoximine, camptothecin, carboplatin, carmustine, estrogen, 5-fluordeoxyuridine, gramicidin D, hydroxyurea, idarubicin, ifosfamide, irinotecan, lomustine, mechlorethamine, mithramycin, mitoxantrone, nitroimidazole, plicamycin, procarbizine, streptozotocin, tenoposide, 6-thioguanine, topotecan, vinorelbine, acyclovir, gangcyclovir, zidovudine, vidarabine, ribavarin, azidothymidine, cytidine arabinoside, amantadine, dideoxyuridine, iododeoxyuridine, poscarnet, or trifluridine.

* * * * *